United States Patent [19]

Rog et al.

[11] 4,322,805

[45] Mar. 30, 1982

[54] ELECTRICAL SURVEY METHOD AND APPARATUS

[75] Inventors: Joseph W. Rog, Medina, Ohio; Karl W. Nicholas, Roselle; Charles G. Waits, Hanover Park, both of Ill.

[73] Assignee: Harco Corporation, Franklin Park, Ill.

[21] Appl. No.: 17,180

[22] Filed: Mar. 5, 1979

[51] Int. Cl.³ .......................... G01V 3/00; G01R 31/02
[52] U.S. Cl. ........................ 364/481; 324/72; 324/323; 346/33 P; 364/420
[58] Field of Search ............... 364/400, 403, 480–483, 364/420, 580, 571, 422; 324/357, 71 R, 72, 329, 323; 360/6; 371/16.25; 346/33 P, 33 WL, 33 D, 33 F

[56] References Cited

U.S. PATENT DOCUMENTS

| | | | |
|---|---|---|---|
| 3,869,707 | 3/1975 | Cupp | 360/6 |
| 3,921,207 | 11/1975 | Doby et al. | 360/6 |
| 4,025,766 | 5/1977 | Ng et al. | 364/403 |
| 4,122,387 | 10/1978 | Ajam et al. | 364/422 |
| 4,136,561 | 1/1979 | Mueller et al. | 360/6 |
| 4,151,458 | 4/1979 | Seager | 324/72 |
| 4,161,782 | 7/1979 | McCracken | 364/571 |
| 4,227,404 | 10/1980 | West | 364/422 |

*Primary Examiner*—Errol A. Krass
*Attorney, Agent, or Firm*—Maky, Renner, Otto & Boisselle

[57] ABSTRACT

An apparatus for making electrical surveys of structures contained in an electrolyte by measuring potential difference therebetween includes an electrode to contact the electrolyte proximate the structure, a wire electrically and mechanically connecting the apparatus with the structure, and an electronic system for automatically electrically sensing and storing the potential difference values taken at a plurality of locations along such structure. In the method for making structure-to-electrolyte potential difference surveys a supply of elongate electrical conductor is electrically and mechanically connected to the structure; the conductor is played out along the structure, and the electrolyte is contacted at plural test locations proximate the structure; and the potential difference at such test location is automatically sensed and stored.

102 Claims, 28 Drawing Figures

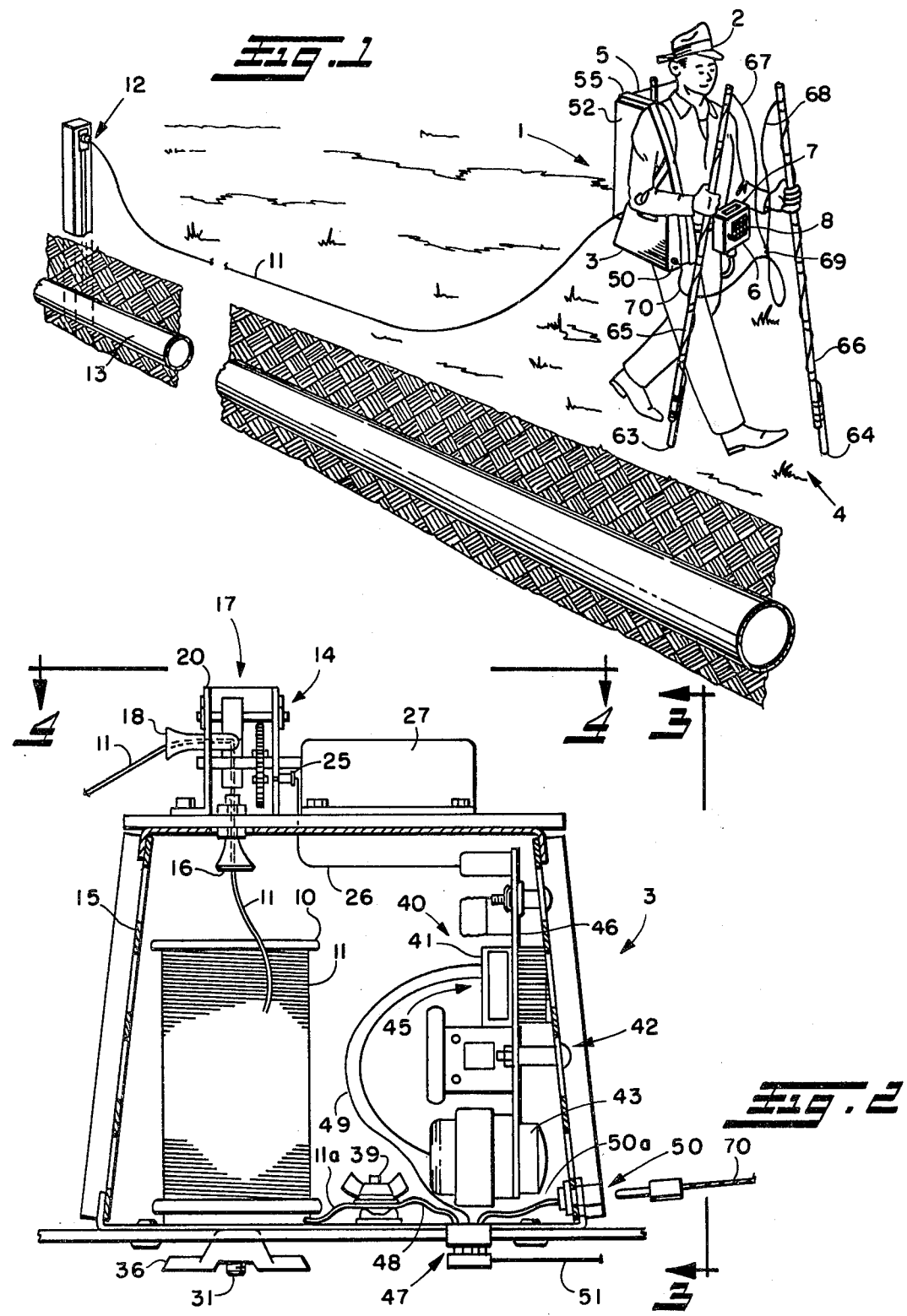

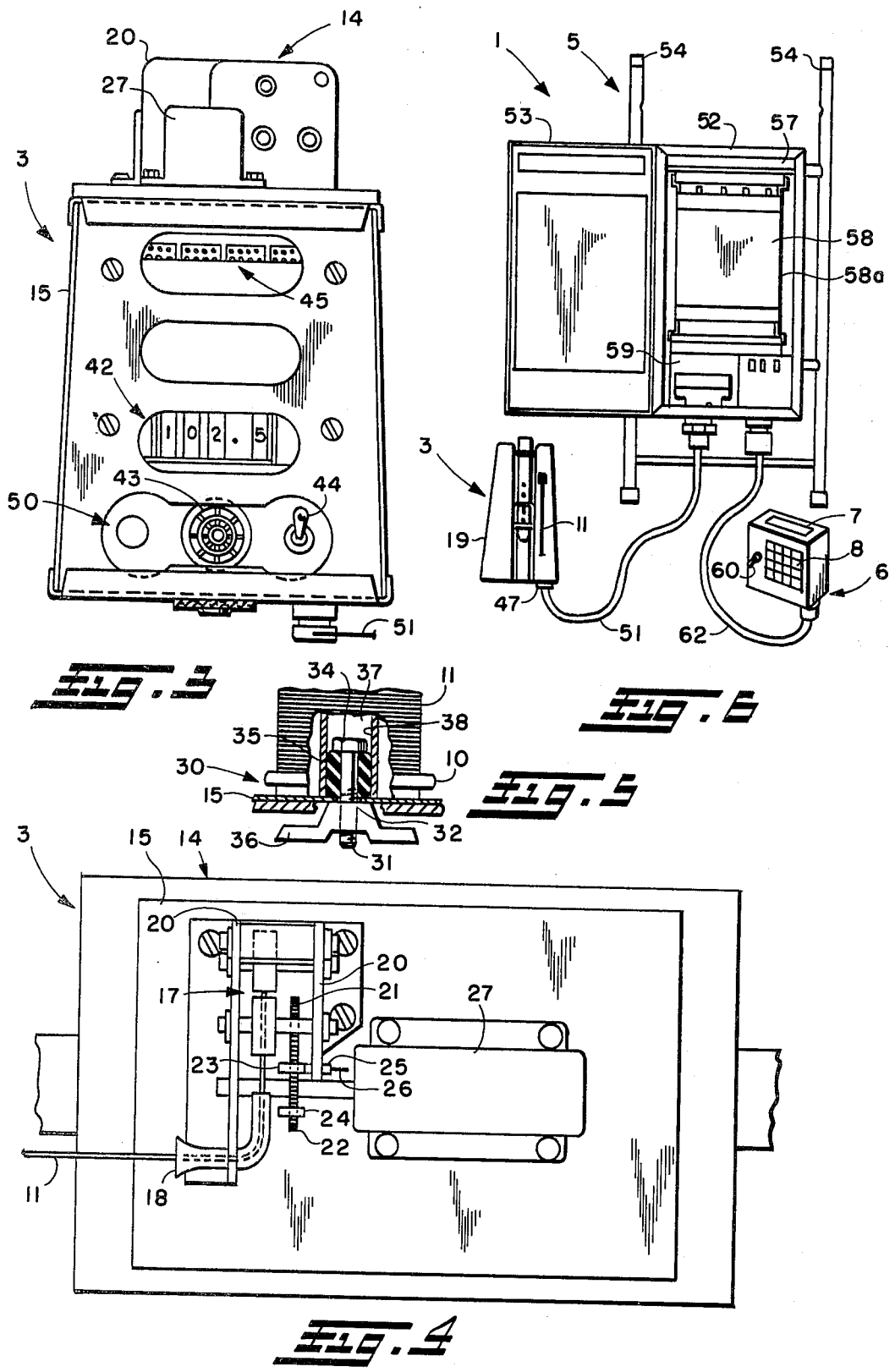

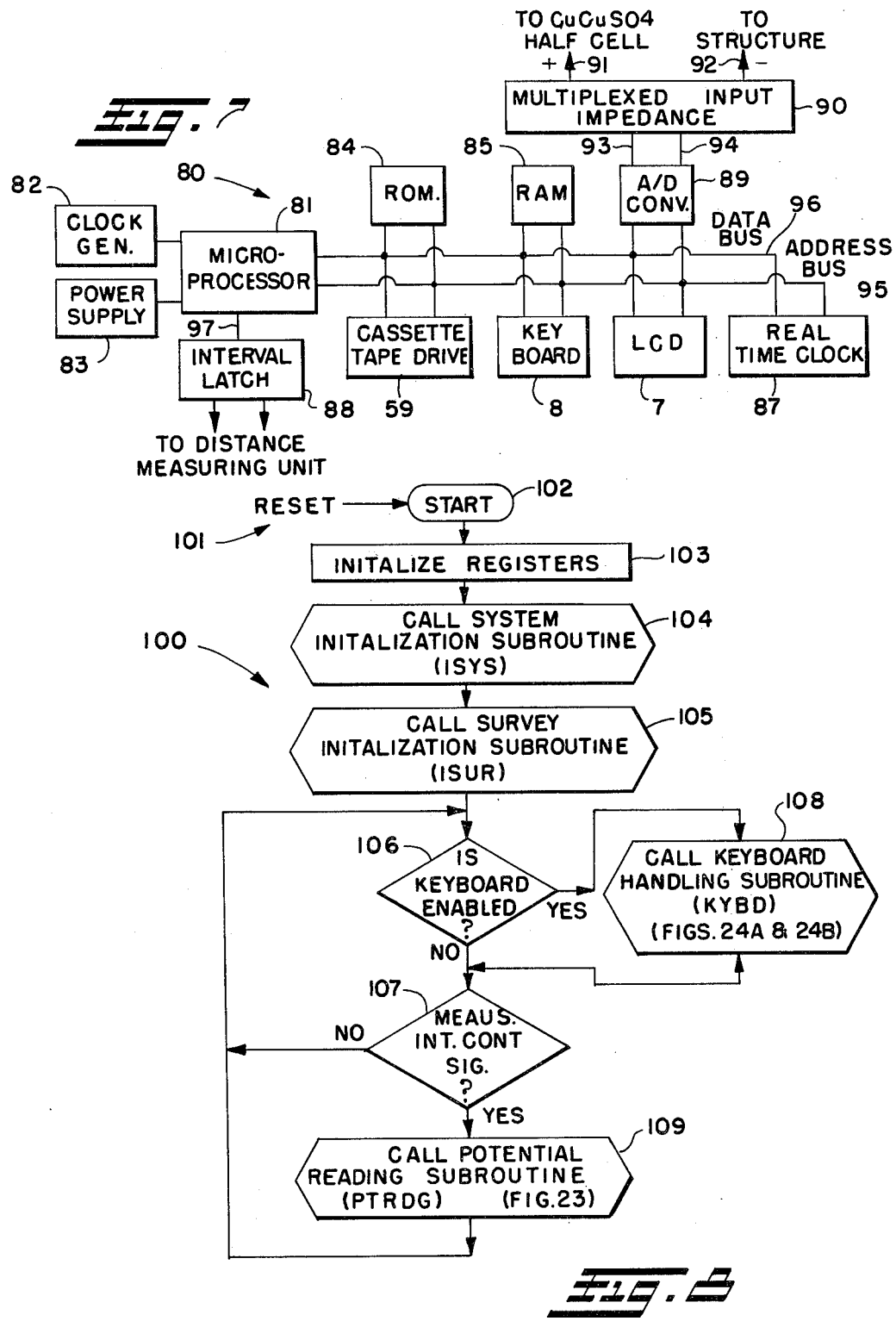

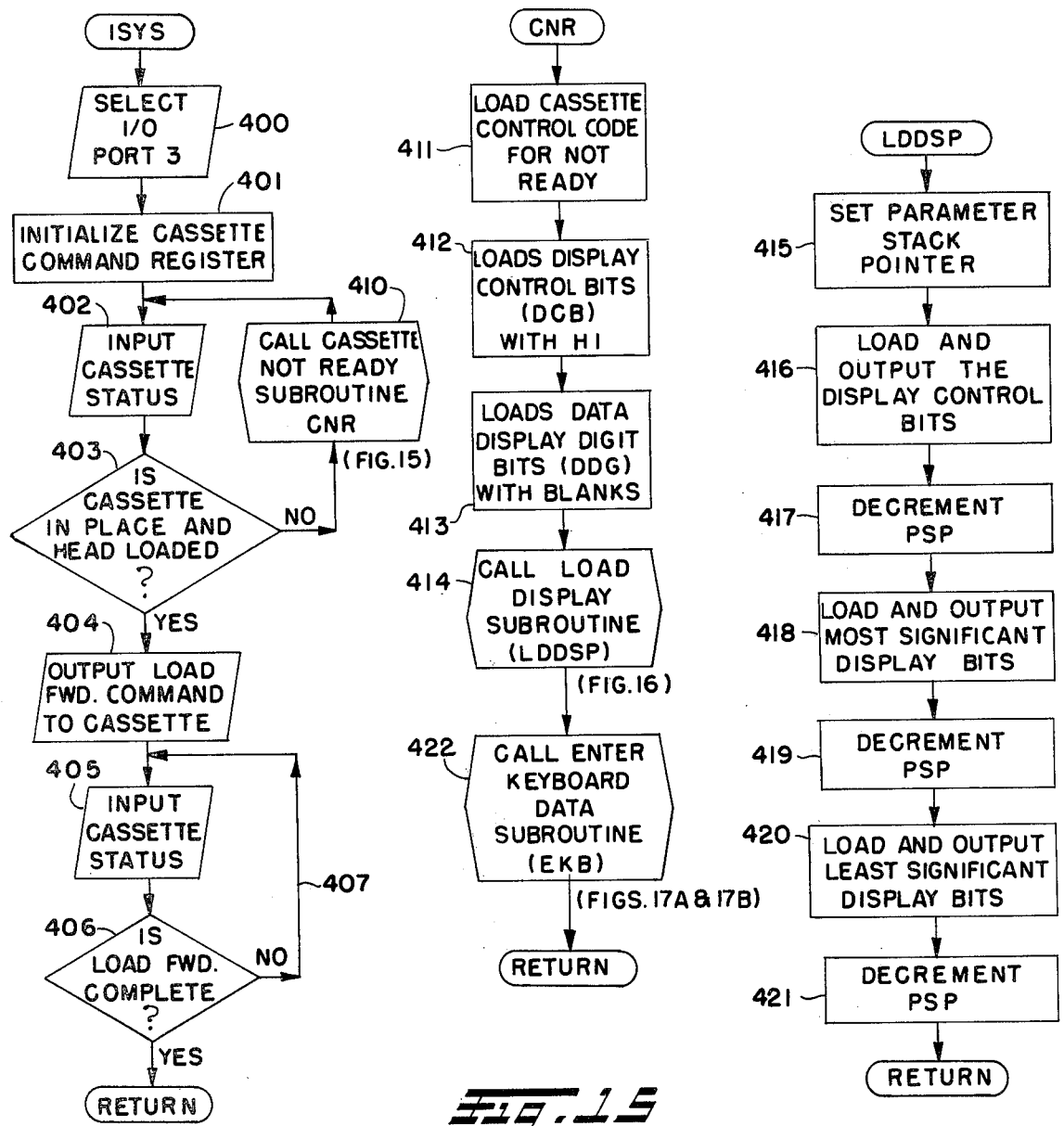

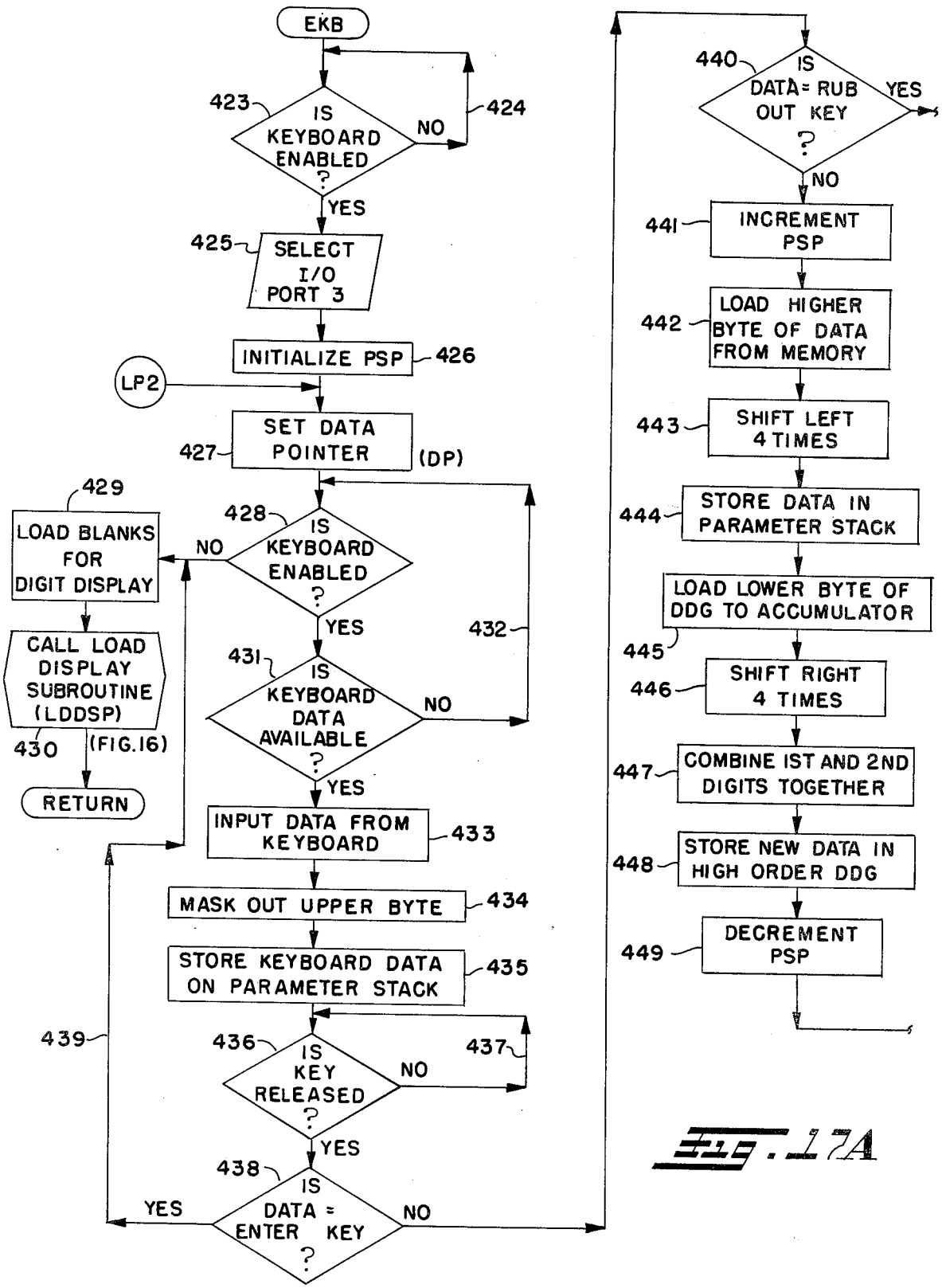

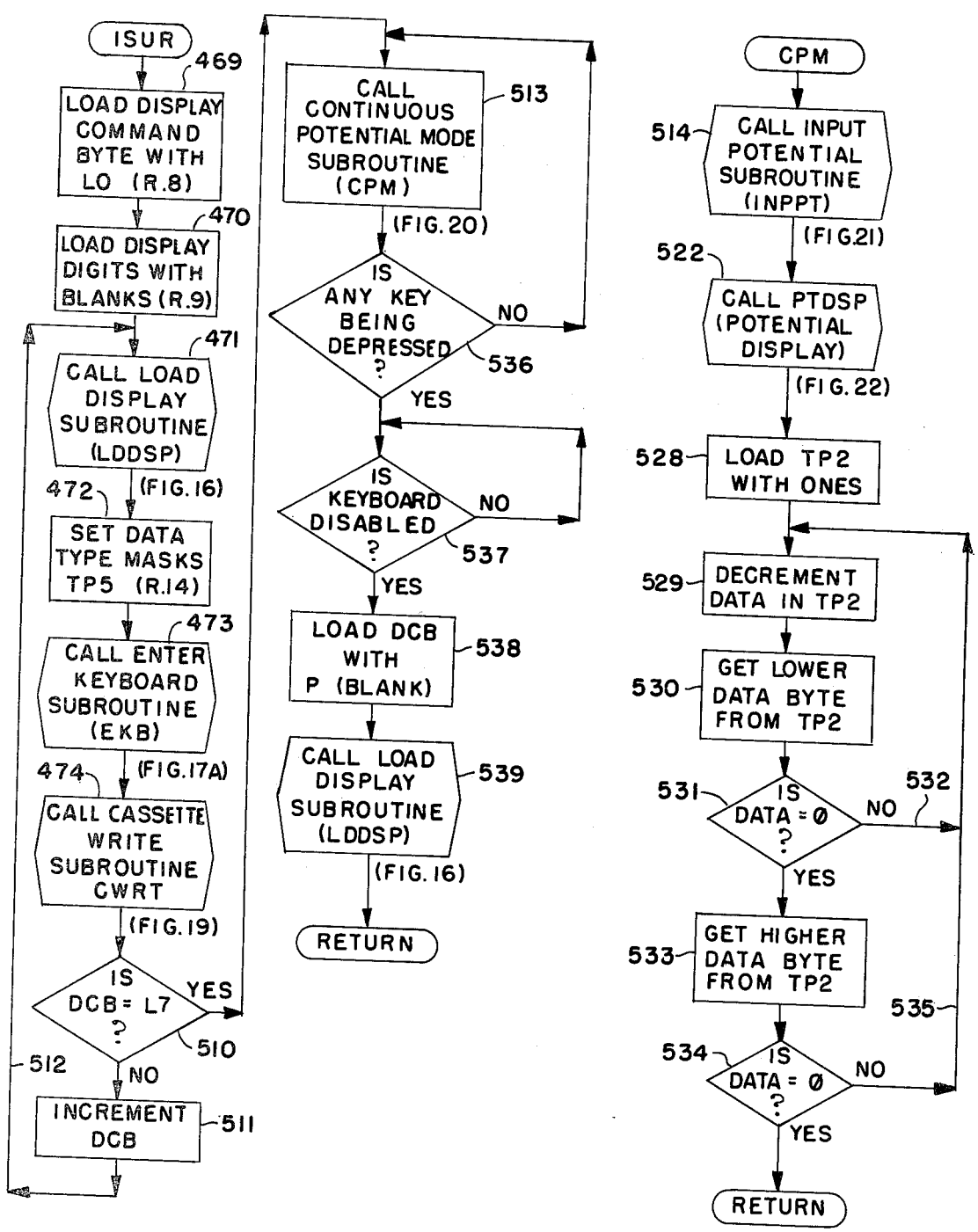

ELECTRICAL SURVEY METHOD AND APPARATUS

TECHNICAL FIELD

The present invention relates generally to electrical type surveys of buried metal structures, such as pipelines or other structures, and, more particularly, to an electrical apparatus and method for making such surveys.

BACKGROUND OF PRIOR ART

In controlling corrosion of pipelines or elongated metal structures buried underground or under water cathodic protection techniques have been employed. The earth or water is an electrolyte. To determine where cathodic protection should be applied and to assure that sufficient cathodic protection voltage is applied to the pipeline, a pipeline survey may be made by taking electrical measurements of the pipe-to-soil potential difference and/or soil resistivity at selected locations along the length of the pipeline. The data gathered in such survey can be analyzed to determine where and/or how cathodic protection can be efficiently employed to prolong the life of the pipeline.

The pipe-to-soil or water potential difference measurement requires a contact to the pipe, a suitable voltmeter or potentiometer, a means of contacting the electrolyte, and connecting wires. A copper-copper sulfate ($Cu-CuSO_4$) cell is an industry standard for providing the necessary contact with the electrolyte. Contact to the pipe usually is provided by a wire connection to a test lead, which is permanently connected to the buried pipe and is brought above ground in a protected, easily accessible location. Such test leads usually are installed along the pipeline from about one to two miles apart. Measurements are commonly made on a yearly basis at the test lead stations to obtain general information concerning the pipeline condition and its relation to the surrounding environment.

However, to obtain more complete data of the pipeline condition a more comprehensive continuous, over-the-pipeline, closely-spaced survey occasionally may be conducted to measure the potential difference, for example, at intervals of, say, 10 to 50 feet along the length of the pipe.

In the past, various techniques have been used to make such relatively closely spaced surveys. In one technique a reel of relatively heavy insulated wire was connected to the pipeline at a test lead, and the wire was dragged from the reel across the ground along the route of the pipeline. The copper-copper sulfate half cell was placed directly over the pipeline at intervals of, say, 10 to 50 feet, and both distance and potential difference measurements were taken and manually recorded. In this technique measurement inaccuracies have occurred due to static electricity accumulation on the dragged wire. Alternatively, the wire was attached to the test lead and the reel was transported by vehicle along the pipeline route. In both cases, though, some form of vehicular transportation was required for the reel and usually powered equipment was required to rewind the wire back onto the reel. Such a system, however, has a number of disadvantages. The reel transporting vehicle and the power-rewinding equipment are heavy, expensive, and consume energy, such as fuel and/or electric power. Several workers were usually required. Since many surveys are made over farm land, crops, etc., and in rough terrain, such as in rocky, mountainous, or wooded areas, across flowing streams, fences, and like impediments, the use of a vehicle often is prohibited or impossible. Also, the physical effort required to drag the heavy wire is considerable, especially when a mile of wire is manually pulled across uneven terrain. The resultant wear on the wire and frequent breakages, plus electric reel maintenance, further add to the cost of such prior systems.

In a recently improved technique for making such relatively closely-spaced surveys a dual function economically disposable, relatively lightweight, flexible wire provides both electrical connection to the pipeline via a test lead and accurate distance measurement information to the surveyor moving along the length of the pipeline. A reel of such lightweight wire is carried by the surveyor, who may walk along the length of the pipeline, and the wire drives a distance measuring unit carried by the surveyor to display the distance from the test station. The surveyor also carries a copper-copper sulfate half cell, which is placed in contact with the ground at selected test locations, and a meter for measuring the potential difference between the wire and the half cell. A single surveyor thus makes both the distance and potential measurements and may write the values in a notebook, verbally recor them on a portable tape recorder, or verbally transmit them by radio for recording at a different location. The wire used for connection to the test lead is not dragged over the ground; rather it is merely laid down as the reel is easily transported along the path of the pipeline. Moreover, the wire is economically disposable and need not be rewound for re-use.

In another recent technique, the supply of wire, distance measuring equipment and electrical measuring equipment are carried by a boat above a submerged pipeline.

The portability of the equipment used in such improved technique facilitates the making of closely-spaced surveys, e.g. by reducing manpower and/or equipment costs over the first-mentioned technique. Also, since the equipment used is highly portable, it can be carried by a single surveyor, for example, even over rough terrains and those over which vehicular travel is prohibited. However, although having a number of advantages over the former techniques described above, nevertheless the distance and electrical information usually is visually read and/or manually recorded.

In addition to the physical problems inherent in older techniques, perhaps the most important consideration with regard to this type of survey is the accuracy of the data collected. The pipeline chaining was often in error from several factors. These would include stretching of the measurement wire from starting and stopping for each reading and inaccurate methods for following the topography of some areas. Also, the value of the galvanic potential developed between the reference electrode and the pipe is one that is much more difficult to measure accurately than is obvious from a superficial understanding. This voltage value can be subject to a high resistance contact at the electrode/earth interface. Therefore, unless a suitable high input impedance voltage measuring instrument is used, many readings would have significant errors. Traditionally, or up to the last two or three years, Potentiometric voltmeters or high resistance D'Arsonval meters have been used. Whatever, they both are quite inferior when compared to contemporary electronic voltmeters (10 meg-ohms are higher input impedance). Another factor that contributed to the voltmeter measurement error is static or friction EMF's generated as the contact wire is pulled along the ground. The polarity of these charges can be positive or negative, but in either case distort the real galvanic voltage.

BRIEF SUMMARY OF INVENTION

The apparatus and method of the present invention facilitate surveys of buried structures, such as pipelines, electrical cables, or the like, in particular by substantially automatically measuring and recording electrical and distance information. Preferably that information is recorded in a form that can be readily manipulated in a computer and displayed, for example graphically, for ease of evaluation. Moreover, the measurements may be made with very small distance intervals between test locations to obtain a substantially continuous survey of the pipeline with much data but without the prior disadvantages of substantially slowing down the survey and increasing the difficulty of data evaluation.

The invention is described relative to surveying a pipeline buried underground. However, the invention also may be used to survey other structures such as cables, and the term pipeline therefore may mean all such structures; and may be used for potential difference, resistivity and other measurements, or with respect to other electrolytes, such as water, and the term soil therefore may mean all such electrolytes.

Briefly, the electrical survey apparatus includes a distance measuring unit (DMU), an electronics package, a keyboard/display unit (KDU), and at least one, but preferably two, means for contacting the ground, such as the conventional copper-copper sulfate half cells. All of these components preferably are relatively lightweight and may be easily carried by a single surveyor walking along the pipeline right of way, or may be transported by vehicle, boat, pack animal, etc. The DMU contains a supply of disposable electrical wires, which is laid down along the pipeline right of way as the surveyor carries the unit therealong, a spinner-type payout or bail out mechanism for the wire, an electronic counter for measuring the length of wire paid out, adjustable input controls for selecting the distance intervals between test locations at which electrical measurements are to be made, a signalling device to advise the surveyor that a measurement is being made, and a reset control. The electronics package includes an electrical supply for the apparatus, a printed circuit card assembly with a microcomputer control, and a tape drive for recording data, all of which preferably are included in a single backpack. The KDU allows the surveyor to input into the microcomputer commands for specific operations and to record pertinent topographical features encountered on the survey and displays the electrical information, such as potential, being recorded, the status of the overall apparatus, including error conditions, and data entered by the keyboard. The half cells are connected in parallel, and during a survey continuous contact with the ground is made by one or the other of the half cells to assure continuous electrical input information to the microcomputer.

According to the method of the present invention, the distance intervals between the test locations are selected, the external end of the disposable wire is connected to a test lead of the pipelines, the system is turned on and reset for operation, and the surveyor walks along the pipeline right of way while also walking the half cells such that at least one of them always is in contact with the ground. Usually there is no need for the surveyor to stop walking during the survey, for the distance information automatically is measured and used to trigger periodic electrical measurements, and the distance and electrical measurement information is recorded automatically. When the surveyor arrives at a subsequent test lead location on the pipeline, he stops; the disposable wire already on the ground may be cut off and left behind and the new end of the disposable wire in the DMU connected to the subsequent test lead so that the survey may be continued, and so on. The KDU may be used to view the electrical values being measured and recorded error codes and feature codes, and to enter commands and features. The survey data obtained preferably is recorded in the electronics package in a computer readable form, for example on a cassette tape in the tape drive. the tape may be removed and delivered to a computer facility at which the data may be reconstructed, say, in graphical form to facilitate evaluation thereof.

In accordance with one aspect of the invention the input impedance of a measuring circuit, which receives the raw potential difference input from the half cells and the pipeline, is changed in a multiplexed manner. This enables checking the integrity of electrical connections and ultimately obtaining a true potential reading, thus improving system accuracy even when large contact resistance between the half cells and the earth is encountered.

With the foregoing in mind, one primary object of the invention is to facilitate the making of electrical surveys of buried metal structures, such as pipelines.

Another primary object is to increase the amount and accuracy of data obtained during such a survey and, therefore, the information value of the survey.

Other objects include the minimizing of the weight of the apparatus for making such a survey and of the power consumption by such apparatus, a corrollary being the increasing of power supply life and the length of pipeline surveyed before rejuvenation of the power supply is required; the providing of versatility, for example, by varying the distance intervals between measurements and by permitting, if desired, plural types of electrical measurements; the facilitating of paying out of the disposable wire; the avoidance of grounding noise encountered in the past under wet conditions, for example; the allowing of such a survey to be made in conditions under which a vehicle transport system could not be used; reducing the cost for such surveys; the minimizing of crop damage; the reducing of time required to make such surveys; and the enabling of several types of measurements to be made and of data analyses to be made.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF DRAWINGS

In the annexed drawings:

FIG. 1 is an environmental view showing a surveyor using the apparatus of the invention to practice the method thereof in surveying a buried pipeline;

FIG. 2 is a side elevation view, partly broken away in section, of the DMU with its cover removed;

FIG. 3 is an end elevation view of the DMU of FIG. 2 looking generally in the direction of the arrows 3—3 thereof;

FIG. 4 is a top view of the DMU of FIG. 2, looking generally in the direction of the arrows 4—4 thereof;

FIG. 5 is a fragmentary section view of the wire spool securing mechanism in the package of FIG. 2;

FIG. 6 is a plan view looking into the power supply and electronics backpack of the apparatus of the invention;

FIG. 7 is a schematic block diagram of the electronic portion of the electrical survey apparatus;

FIG. 8 is a flow chart block diagram depicting operation of the electrical survey apparatus in carrying out the method of the invention;

FIGS. 14 through 26 are partial flow chart block diagrams depicting in connection with FIG. 8 the best mode of practicing the invention.

DESCRIPTION OF THE PREFERRED EMBODIMENT

Figure 9:
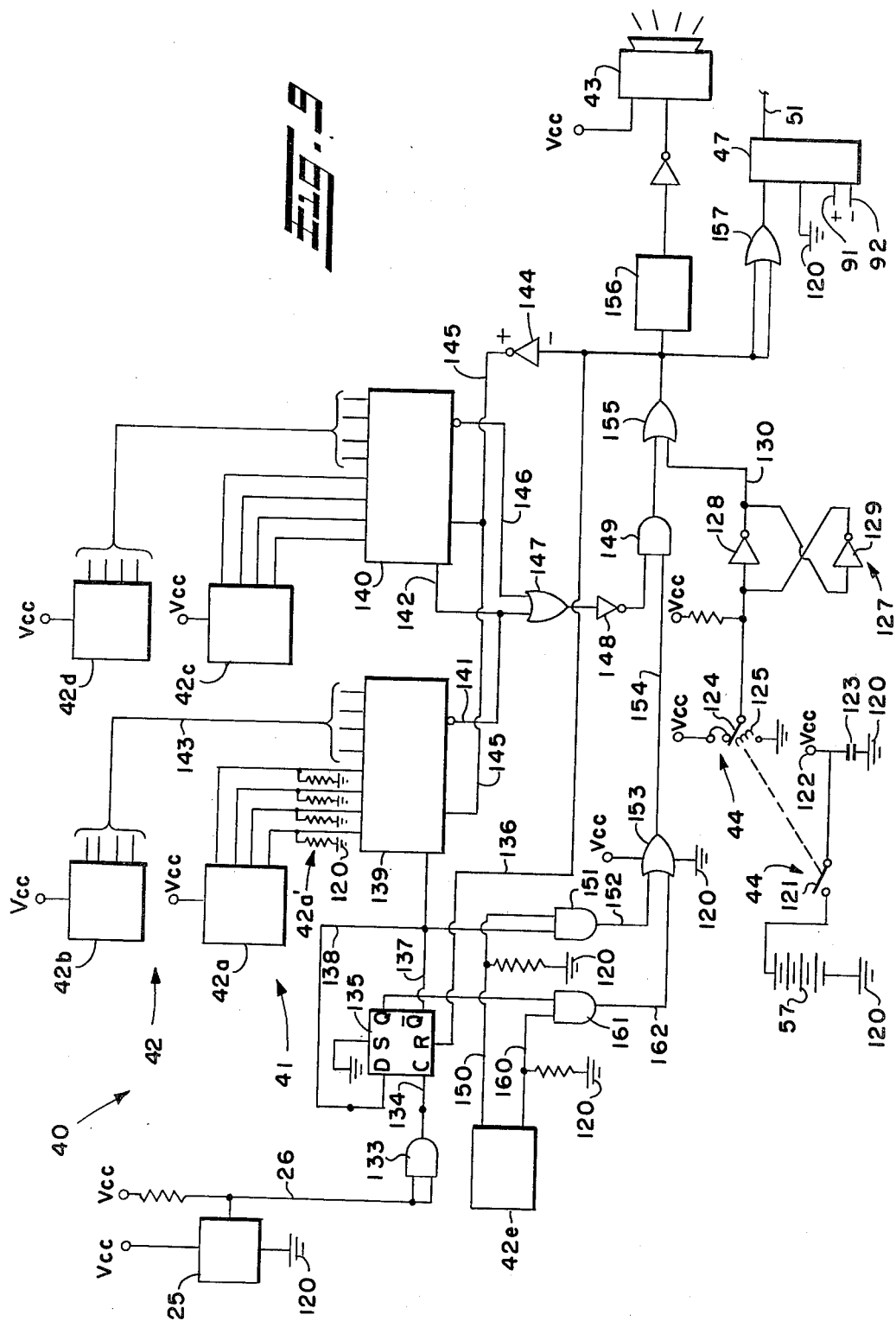
FIG. 9 is a schematic electric circuit diagram of the distance measuring circuit of the invention.

Referring now in detail to the drawings, and initially to FIGS. 1-6, an electrical survey apparatus in accordance with the present invention is generally indicated at 1. The electrical survey apparatus preferably is intended to be carried and operated by a single surveyor 2 and, accordingly, is relatively lightweight, conveniently portable, durable, and efficiently utilized. The apparatus 1 includes a distance measuring unit 3 (DMU), one, and preferably two, electrical potential contacting devices 4, a power supply, electronic measuring circuitry, and tape drive all contained in a power supply and electronics backpack 5, and a keyboard/display unit 6 (KDU) preferably with a conventional visual display 7 and keyboard 8.

The DMU 3 includes a spool or other supply 10 (FIG. 2) of relatively lightweight, insulated, disposable wire 11, preferably copper, that provides two functions. One function of wire 11 is the provision of an electrical connection via a conventional test lead 12 to a buried metal pipeline 13. The other function of wire 11 is to drive a distance measuring mechanism 14 which generates electrical information indicative of the length of wire paid out from the spool 10.

The spool 10 is mounted in a metal frame 15 to deliver wire 11 to the distance measuring mechanism 14 with a spinner type action, i.e. like a conventional spinner type fishing line reel. Since the spool 10 does not rotate, the possibility of its binding and resulting wire breakage is eliminated and the integrity of the electrical connection of the wire 11 to the electrical measuring circuitry of the system 1 is maximized. A funnel 16 directs the wire 11 as it spins off the spool 10 into the distance measuring mechanism 14 where the wire is passed over a friction drive wheel assembly 17 and through a guide pipe 18 from which it leaves the DMU 3. The frame 15 is supported in an electrically non-conductive case 19 of the DMU and the electrical circuits in the DMU are insulated from the frame to avoid grounding noise through the surveyor.

The distance measuring mechanism 14 includes support frame 20 on which a drive gear 21 is mounted to be rotated by the drive wheel 17 to rotate therewith. Moreover, the drive gear 21 rotates a sensor gear 22, as is seen most clearly in FIG. 4. Mounted in the sensor gear 22 is a pair of magnets 23, 24, which rotate past a Hall effect switch pick-up 25 sequentially at a speed determined by the rate at which the wire 11 is paid out from the DMU 3. Leads 26 couple pulses produced in the pick-up 25 as the respective magnets 23, 24 rotate past such pick-up to electronic measuring circuitry in the DMU 3. A conventional mechanical counter 27 may be connected to the sensor gear 22 to provide a visual indication of the length of wire 11 paid out.

The spool 10 may carry up to several miles length of wire 11 due to the small gauge and light weight of such wire. Preferably the wire 11 has a lacquer or plastic type insulation to prevent electrical connection with the ground, metal fences, or the like as it is layed down while the surveyor walks along the ground above the pipeline 13 to conduct a survey. The spool 10 is securely mounted, but easily removable for replacement, when necessary, in the DMU 3 by a friction holding mechanism 30 (FIG. 5). The friction holding mechanism 30 includes a threaded bolt 31, which extends through an opening 32 in the base of the metal frame 15, a head 34 on the bolt, a rubber or other resilient elastomeric material cylinder or washer 35 on the bolt between the head 34 and the frame 15, and a wing nut or other tightener 36 on the bolt 31. The head 34 of the bolt 31 and a substantial portion of the rubber cylinder 35 extend within the hollow central volume 37 of the spool 10 defined by a cylindrical wall 38 of the spool. With the spool 10 positioned over the cylinder 35, tightening of the wing nut 36 will draw the bolt head 34 toward the frame 15 to expand the rubber cylinder 35 against the spool wall 38 thereby securely to hold the spool 10 in fixed position in the distance measuring unit 3.

One end of the wire 11 extends outside of the DMU 3. The other end of the wire 11 is connected by a pigtail portion 11a thereof to an insulated terminal post 39 (FIG. 2).

A distance measuring circuit 40 in the DMU 3 receives pulses on lead 26 from the Hall effect switch pick-up and converts those pulses to electrical information indicating the length of wire 11 paid out and, thus, the distance the surveyor 2 has walked along the ground above the pipeline 13 away from the test lead 12. The distance measuring circuit 40 includes a measuring interval control circuit 41 with a plurality of thumb wheel switches 42 or other means that can be set manually by the surveyor 2 to establish the distance intervals at which potential difference measurements will be taken by the apparatus 1. Typically, such distance intervals may be as small as one-half foot to as large as several hundred feet, as desired. Preferably, however, for optimum efficient use of the electrical survey apparatus 1, the distance intervals will be on the order of 2½ to about 50 feet. The distance measuring circuit 40 produces a measuring interval control signal each time a length of wire 11 equal to the distance interval set on the thumb wheel switches 42 has been paid out from the DMU 3 to cause the electronic circuitry in the backpack 5 to take and to record a potential difference measurement. A horn 43 also is energized briefly in response to each measuring interval control signal to indicate that a potential measurement is being taken, and a reset switch 44 may be selectively operated by the surveyor 2 to reset the distance measuring circuit 40 when commencing a survey operation.

Several integrated circuits 45 of the measuring interval control circuit 41, as well as the horn 43 and reset switch 44, are mounted on one or more printed circuit boards 46 in the DMU 3. A multiconductor connector 47 receives the pipe potential signals from wire 11 and terminal 39 via lead 48; the measuring interval control signals from the distance measuring circuit 40 via lead 49; and the soil potential signals from the contacting devices via a banana plug 50 and lead 50a. A multiconductor cable 51 couples such signals to the electronic circuitry in the backpack 5.

The backpack 5 includes a metal housing 52 with a hinged door 53 supported on the back and shoulders of the surveyor 2 by a metal framework, preferably of lightweight aluminum poles 54 and strips 55. Within the housing 52 are an electrical power supply 57 for the apparatus 1, electronic circuitry 58 most of which preferably is on printed circuit boards mounted in a card cage 58a, and a cassette tape drive or other recorder 59. The power supply 57 preferably includes two rechargeable batteries such as 12 volt 2.5 AH Gates #0810-0016 lead acid batteries, for positive and negative supply purposes relative to a common ground capable of providing power to the apparatus 1 for up to about twenty hours. The power supply 57 also may be coupled via cable 51 to supply power to the distance measuring circuit 40. The electronic circuitry 58, which will be described in more detail below with reference to FIGS. 9-13, effects electronic measuring of potential difference signals and control of the tape drive 59 for storage of data concerning such signals, the locations at which potential difference measurements are taken, and general feature information, such as the client for whom the survey is to be made, topographical obstructions in the path of the survey, etc. The recorder 59 preferably is a Memodyne 933 tape drive that is operated in an incremental mode only when called on, thereby conserving power, to store digital information concerning the survey on a magnetic tape.

The KDU 6, which may be selectively activated and deactivated by the throw of a switch 60, includes a conventional hexadecimal (16 key) keyboard 8. By pressing respective keys the surveyor 2 may enter keyboard data such as command data to command certain operation of the electronic circuitry 58 or feature data concerning the nature of the survey, e.g. the pipeline owner, survey date, location of obstructions like fences and streams, etc., for storage by the tape drive 59. The KDU 6 is connected to circuitry 58 via a cable 62. The visual display 7 preferably is a liquid crystal type display that is energized by signals from the electronic circuitry 58 delivered through the cable 62 to indicate potential difference measurements being made automatically by the electrical survey apparatus 1, keyboard data entered through the keyboard 8, etc.

Each of the electrical potential contacting devices 4 includes, for example, a copper-copper sulfate half cell electrode 63, 64 attached to a non-metallic cane 65, 66. An electrical lead 67, 68 from each half cell is taped to a respective cane, and the leads are joined at a mechanical and electrical connection 69 so that the half cells are effectively in electrical parallel. A further lead 70 delivers the soil potential signals via the banana plug connector 50 and wire 50a to connector 47.

In operation of the electrical survey apparatus in accordance with the method of the present invention, a surveyor 2 would mount the DMU 3, backpack 5, and KDU 6 on his person, for example as shown in FIG. 1. The surveyor 2 also would connect an end of the wire 11 to the test lead 12, would adjust the thumb wheel switches 42 for a desired distance interval between successive potential difference measurements to be made by the electrical survey apparatus 1, and with the keyboard 8 enabled by the switch 60 would enter into the keyboard certain identifying information concerning the survey, as aforesaid. Thereafter, the switch 60 would be thrown to disable the keyboard 8, and the surveyor would briefly throw the reset switch 44 to reset distance measuring circuit 40 in preparation for starting the survey. Then, the canes 65, 66 are taken in hand to hold the half cells 63, 64 in contact with the soil. The surveyor 2 then walks along the ground above the pipeline 13 while also walking the canes and half cells preferably assuring that at least one half cell always is in direct contact with the soil. As the surveyor walks, the wire 11 is paid out from the DMU 3, and each time a distance interval equal to that set on the thumb wheel switches 42 is paid out, and, accordingly, walked by the surveyor, a measuring interval control signal briefly energizes the horn 43 and causes the electronic circuitry 58 to measure the potential difference between the soil potential signal on line 50a from one or both half cells 63, 64 and the pipe potential signal from the wire 11. The datum concerning the magnitude of such potential difference signal is recorded in the tape drive 59.

The audible signals from the horn 43 indicate to the surveyor that measurements are being taken by the electrical survey apparatus in an automatic fashion and their repetition rate also indicates the speed at which the surveyor is making the survey.

Since the distance and electrical data are measured and recorded automatically, since the wire 11 is lightweight, long, and disposable, the latter eliminating the need for rewinding, and since the battery 57 has a substantial storage capacity, large distances may be covered by the surveyor 2 in making an effective survey without having to replace or recharge the battery, replace the wire 11, reconnect to a subsequent test lead 12, etc., thus improving the efficiency with which such pipeline surveys can be made. Also, since the surveyor 2 can cross difficult terrain or obstacles, such as fences, crop fields, streams, etc., quite effectively, especially relative to the ability of heavy vehicles to do so, the efficiency with which a survey can be made is further increased.

The data obtained by the apparatus 1 is recorded preferably in a digital format by the tape drive 59. That data may be extremely abundant when very small distance intervals are used and is readily adaptable for computer analysis in an extremely efficient manner to provide output information in a variety of formats, including quantitative, graphical, comparative, and other formats. This ability further optimizes the value and use of the survey information for maximum efficiency in cathodically protecting the surveyed pipeline, including, for example, not only analysis of data taken during a recent survey but also an historical comparison with that data taken in the past.

After a survey has been completed, end of survey information can be entered to the tape drive 59 via the keyboard 8. The magnetic tape cassette then can be removed and forwarded to a computer installation for data analysis, thus facilitating such analysis.

In view of the foregoing, it will be clear that the electrical measurements taken by the electrical survey apparatus will be extremely accurate, because, on the one hand, such measurements are taken automatically and, on the other hand, such measurements are taken at relatively accurately defined intervals defined electronically by the measuring interval control circuit 41 regardless of the speed at which the surveyor 2 walks along the path of the pipeline 13.

Turning now to FIG. 7, a schematic block diagram of the electrical portions of the apparatus 1 is illustrated. The apparatus 1 includes a microcomputer 80 with a plurality of input/output interfaces coupled to peripheral equipment. The microcomputer 80 includes a microprocessor 81, a high frequency clock generator 82, a power supply 83, which may be of the regulator type receiving unregulated input power from the power supply battery 57, a read only memory (ROM) 84, and a random access memory (RAM) 85. The peripheral equipment to which the microprocessor 81 is coupled includes the tape drive 59, the keyboard 8 and liquid crystal visual display 7 of the KDU 6, and a real time clock 87, which indicates the actual time of day, for example. Other peripheral devices or equipment coupled to the microprocessor 81 include an interval latch circuit 88, which receives the pulses of the measuring interval control signal from the distance measuring circuit 40, and an analog-to-digital (A/D) converter circuit 89. A multiplexed input impedance circuit 90 is coupled, as indicated, to receive on leads 91, 92, which connect with cable 51, the pipe potential signal and soil potential signal, respectively. The circuit 90 described in detail with reference to FIG. 11 further improves the accuracy of the potential difference measurements made by the apparatus 1 primarily by compensating for high resistance contact between the reference cells 63, 64 and the earth. The A/D converter 89 converts the analog potential difference signal on lines 93, 94 at the output of the circuit 90 to digital information which can be processed by the microprocessor 81 and stored via the tape drive 59. The microprocessor 81 is coupled by an address bus 95 and a data bus 96 to certain peripheral devices, as shown, and is connected by a line 97 to receive measuring signals from the interval latch 88 that determine when the digital value of the difference between the pipe and soil potential signals is to be sensed, measured and stored.

In FIG. 8 is a flow chart 100 representing the method of operation of the electrical survey apparatus 1 under control of the microcomputer 80. In accordance with conventional computer programming techniques, the flow chart 100 may be reduced to computer program information that may be stored, for example, in the ROM 84 to effect such controlled operation of the apparatus 1. Several subroutines are noted in the flow chart 100, and these will be described briefly below.

When a surveyor briefly throws a reset switch 44a (FIG. 10) to its reset position, noted at 101 in the flow chart 100, the system 1 starts operation, block 102. Accordingly, the various registers in the microcomputer 80 are initialized in conventional manner, block 103, and then a system initialization subroutine is called, block 104, to initialize the peripheral devices coupled to the microcomputer 80. The system initialization subroutine 104 primarily initializes the tape drive 59 to assure that the cassette is in place, the head is loaded, and the cassette is ready to operate in a load forward mode; the system initialization subroutine 104 also initializes the display 7, keyboard 8, and A/D converter 89.

After such system initialization, a survey initialization subroutine is called, block 105. The survey initialization subroutine 105 is used to input data from the keyboard 61 for company name, e.g. pipeline owner, pipeline to pipeline location being surveyed, direction of survey, and operator or surveyor identification.

After completing such initialization procedures, the flow chart 100 enters a loop whereby the microcomputer 80 continues to look for a signal indicating that the keyboard 8 is enabled, block 106, or a measuring interval control signal indicating that a potential difference measurement should be made, block 107. If the keyboard 8 is enabled, block 106, by the switch 60, then a keyboard handling subroutine, block 108, is called to enable entry of information from the keyboard 8 into the microcomputer 80. When the keyboard is so enabled, the keyboard data or information entered from the keyboard ordinarily is displayed in the display 7. When a measuring interval control signal pulse is received, block 107, a potential reading subroutine is called, block 109, whereupon the apparatus 1 effects a potential difference measurement, stores the data obtained concerning such measurement, and returns to point 110 in the illustrated flow chart loop. A more comprehensive description of the steps illustrated in the flow chart will be described in more detail below in connection with FIGS. 14–25.

Turning now in detail to FIG. 9, the distance measuring circuit 40 is shown in detail. Such circuit is described in further detail in copending, commonly assigned U.S. patent application Ser. No. 972,041, filed Dec. 21, 1978, for "Electrical Survey Apparatus and Method With Automatic Distance Measuring", the disclosure of which is hereby incorporated by reference. Electrical power for such circuit is provided by the battery 57, which has its negative terminal connected to a source of ground reference potential 120, the symbol of which is used throughout the circuit diagrams of this application, and the positive terminal of which is connected via a switch arm 121 of the reset switch 44 to a regulated $V_{cc}$ power terminal 122. A capacitor 123 provides conventional filtering for the $V_{cc}$ power signal. Other exemplary $V_{cc}$ power connections, which receive power from the terminal 122, are similarly identified by the letters $V_{cc}$ throughout the drawings of this application. The reset switch 44 also includes a movable switch arm 124 and a spring 125. The reset switch 44 is a threeposition switch, as follows: in one position, the off position, the switch arm 121 is open, and the switch arm 124 is connected, as shown in FIG. 9; in the on position the switch arm 121 is closed, as shown in FIG. 9, and the switch arm 124 also remains, as shown in FIG. 9, connected to receive a $V_{cc}$ power signal; in a reset position of the switch 44, which is an unstable position resisted by the spring 125 back toward the on position, the switch arm 124 may briefly be held manually in connection with the source of ground reference potential 120 to effect the resetting of a conventional debouncing circuit 127. The circuit 127 includes two inverting amplifiers 128, 129 which upon being reset produce a positive reset signal on line 130. It is the purpose of such reset signal to effect energization of the horn 43 and a resetting of the counters, which are described below, of the measuring interval control circuit 41. After the switch 44 is released to "on", the system 1 will be ready to operate as described in detail below.

In the distance measuring circuit 40 the Hall effect switch pick-up 25 (FIG. 4) produces on line 26 a series of electrical pulses having a frequency equal to twice the rotational frequency of the sensor gear 22 since there are two magnets in the latter. Preferably, the size of the sensor gear 22 and the gear ratio thereof with respect to the drive gear 20 are selected such that a separate pulse is produced on line 26 each time 0.5 ft. of wire 11 has been paid out through the friction drive wheel 17 and guide pipe 18. The pulse train on line 26 passes through a buffer AND gate 133 and from the latter via line 134 to a D type toggle flip-flop circuit 135. When the flip-flop 135 is reset by a signal on line 136, the Q output goes low. Thereafter, the Q output will go high upon receipt of the first pulse on line 134, will go low upon receipt of the next pulse on line 134, etc. Therefore, whenever the Q output is high, it is indicative of a 0.5 foot, 1.5 feet, etc., of wire having been paid out, whereas each time the $\overline{Q}$ output is high, it is indicative of a whole number of feet having been paid out from the distance measuring unit 3.

The $\overline{Q}$ output of flip-flop 135 is connected by line 137 in a feedback path via line 138 and to a clock input of a binary coded decimal programmable down counter 139, such as an RCA integrated circuit number CD40102BE. A similar binary coded decimal programmable down counter 140 is connected to the output line 141 of the counter 139 to receive clock signals on line 142 therefrom each time counter 139 reaches zero. The thumb wheel switches include four conventional thumb wheel switch assemblies, such as those manufactured by Cherry Manufacturing, 42a–42d, which may be adjusted to set 1's, 10's, 100's, and 1000's, respectively, values from which the counters 139, 140 will count down in conventional manner in response to clock signals input thereto. Four lines shown connected between thumb wheel switch 42a and counter 139 are respectively high or low logic signal values, depending on the setting of the switch 42a, by making connections to the $V_{cc}$ supply or to ground, for example through resistors 42a' illustrated with respect to switch 42a, to program the counter to a value from which it must count down in response to clock signals input from line 137. Four lines similarly connect the thumb wheel switch 42b and resistors, not shown, like those at 42a', to the counter 139 for the same purpose; it is noted here that throughout this application for convenience of illustration wherever parallel lines are to be connected a pair of brackets and a common single line connector such as the one shown at 143 will be illustrated. The thumb wheel switches 42c and 42d are similarly connected to program the value from which the counter 140 will count down in response to clock signals received on line 142. The counters 139, 140 may be reset by a signal from inverting amplifier 144 and line 145 effectively to store the respective values set in the thumb wheel switches 42 from which the counters will count down in response to respective clock signals thereto. When both counters 139, 140 have counted down to a predetermined value, as desired, such as zero such that the signals on their output lines 141, 146 are logic zero levels, a logic zero signal will be produced by OR gate 147 and inverted to a logic one signal by inverting amplifier 148 for delivery to an AND gate 149. The signal produced by inverting amplifier 148 is in effect a preliminary footage signal which indicates that the desired whole number footage of wire 11 as set in the thumb wheel switches 42 has been paid out from the distance measuring unit 3.

The thumb wheel switches 42 also include a further thumb wheel switch 42e, which is used to determine whether the footage or magnitude of the distance interval at which measurements are to be taken is to be a whole number or a fractional number. Specifically, the thumb wheel switch 42e may be adjusted to provide a high signal on line 150 so that each time a Q output of the flip-flop 135 goes high, which indicates a whole number of feet having been paid out from the distance measuring unit, a positive signal is produced by AND gate 151 on line 152, and that positive signal is delivered by OR gate 153 and line 154 to the other input of AND gate 149, whereupon the latter will produce a measuring interval control signal via an OR gate 155. Such control signal triggers a one-shot multivibrator 156 that energizes the horn 43 for a predetermined duration and is passed by OR gate 157 and connector 47 to the electronic circuitry 58 to effect measurement of the potential difference signal. Alternatively, when the thumb wheel switch 42e provides a high signal on line 160, an AND gate 161 will produce a high signal on line 162 each time a 0.5 ft. length of wire 11 has been paid out from the distance measuring unit 3 to energize the AND gate 149, as aforesaid, until the next data pulse is received by flip-flop 135.

As used herein, the terms logic one, positive and high signal mean the same and logic zero, negative and low signal mean the same.

Summarizing operation of the distance measuring circuit 40, then, the thumb wheel switches 42 are manually set to a desired measuring interval of from 0.5 ft. to 9999.5 ft. Upon operating the reset switch 44 to reset such circuit, a reset signal on line 130 causes energization of the one-shot multivibrator 156 to operate the horn 43 and resets the counters 139, 140 via the inverting amplifier 144 and line 145. Thereafter, as the surveyor 2 walks over the pipeline 13, a plurality of pulses will be produced on line 132 causing counting down by the counters 139, 140. Each time the desired length of wire 11 has been paid out from the DMU 3, as set on the switches 42, a measuring interval control signal from OR gate 155 also will effect energizing of the horn 43, another resetting of the counters 139, 140 to the values set on the thumb wheel switches 42a–42d, and, through OR gate 157, operation of the electronic circuitry 58 to take a potential difference measurement and to record the data concerning the same.

Figure 10:
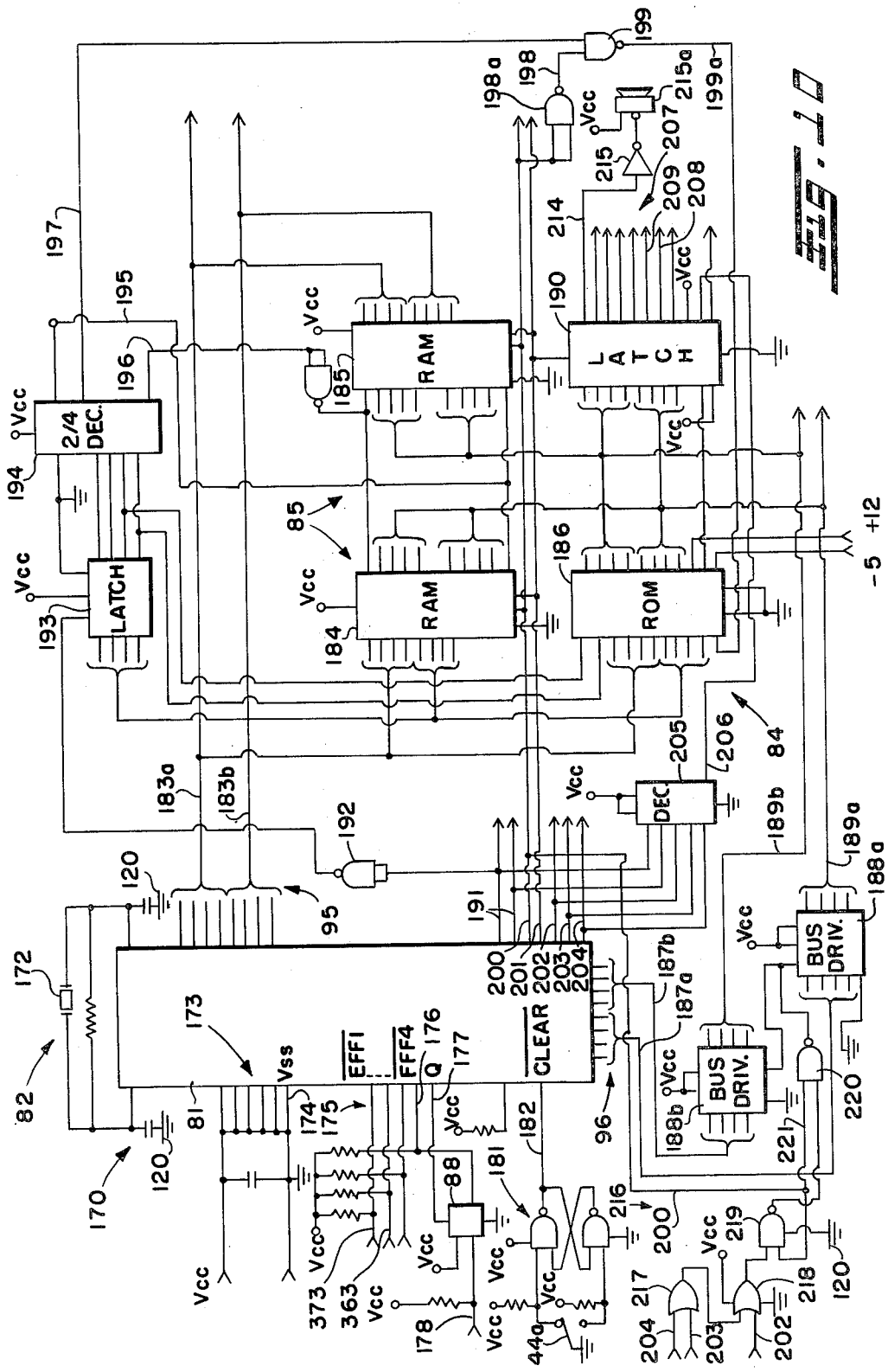
FIG. 10 is a schematic electric circuit diagram of the central processor unit (CPU) and its directly associated electronic circuitry of the invention.

In FIG. 10 is illustrated the central processor unit (CPU) 170 and associated circuitry 171 of the electronic circuitry 58. The CPU 170 preferably is an integrated circuit microprocessor 81 Model No. CDP1802 of RCA. A 2.000 MHz clock signal generator 82, which includes a crystal oscillator 172, is coupled to provide clock signals to the CPU 170. A number of input terminals, such as the $V_{DD}$, $V_{CC}$, $\overline{WAIT}$, etc., indicated at 173 are connected to the $V_{cc}$ power supply, and the $V_{ss}$ terminal 174 is connected to the ground reference potential 120. Moreover, a number of input ports 175, such as those typically identified by the designations $\overline{\text{EF1}}$, $\overline{\text{EF2}}$ and $\overline{\text{EF3}}$, are connected to be tested by software, and the input terminal 176 ($\overline{\text{EFF4}}$) is connected by line 177 to the interval latch 88, such as a D type flip-flop, which receives on line 178 as clock signals the measuring interval control signals from the cable 51, connector 47 and OR gate 157 (FIG. 9). Thus, the signal delivered on line 176 to the microprocessor CPU 170 will cause the latter to operate the electronic circuitry 58 to effect a measurement and recording of the pipe-to-electrolyte potential difference. A pulse on the Q output 177 of the CPU 170 will reset the flip-flop 88 after completion of such individual measurement and recording.

The reset switch 44a may be briefly manually closed to provide power via a debouncing latch circuit 181 to reset the electronic circuitry 58. The reset signal is provided on line 182 to the $\overline{\text{CLEAR}}$ input of the CPU 170 to prepare the same for operation, for example upon power up, at the start of a survey, or after correcting a fault as described below, by directing the CPU 170 to the start 102 of its program (FIG. 8).

The address bus 95 is coupled from the CPU 170 in two respective groups of four lines, 183a, 183b to a pair of RAM integrated circuits 184, 185, such as RCA integrated circuits Nos. CDP1822. The address bus 95 also is connected to a ROM 186, such as an INTEL EPROM integrated circuit No. B2708L. The data bus 96 from the CPU 170 is connected by two groups of four lines 187a, 187 b to respective conventional bus driver circuits 188a, 188b (RCA No. CDP1856) and via the latter to the RAMS 184, 185 and ROM 186 via lines 189a, 189b. The data bus also is connected to an eight bit output latch circuit 190 to select respective I/O ports, such as individual circuit boards containing controls for the tape drive 59, KDU 6, and A/D converter 89. The CPU 170 produces timing pulses at output ports coupled to timing lines 191 to control certain circuits, as illustrated, such time pulses on lines 191 indicating where the CPU is in its machine cycle at any time. A NAND gate 192 coupled to one of the timing lines 191 controls operation of a latch circuit 193, which receives only the lower four bits from the address bus 183b and provides the latched in data to a dual two of four decoder 194 which decodes the address information to indicate whether information is to be written into one of the RAMs 184, 185 or read from the ROM 186. The latch circuit 193 may be an RCA integrated circuit No. CD4076 and the dual two of four decoder 194 may be an RCA integrated circuit No. CD4555. Accordingly, a signal on either of lines 195, 196 will enable the RAMs 184, 185. A high signal on line 197 as well as on line 198 at the output NAND gate 198a, which is directly controlled by CPU 170, will cause NAND gate 199 to effect a chip select function for ROM 186 via line 199a.

Moreover, memory read signals are provided on line 200 from the CPU 170, and memory write signals are provided on line 201 from the CPU 170 for controlling operation of the RAMs 184, 185 in particular, and additionally the latch 190.

Figure 11:
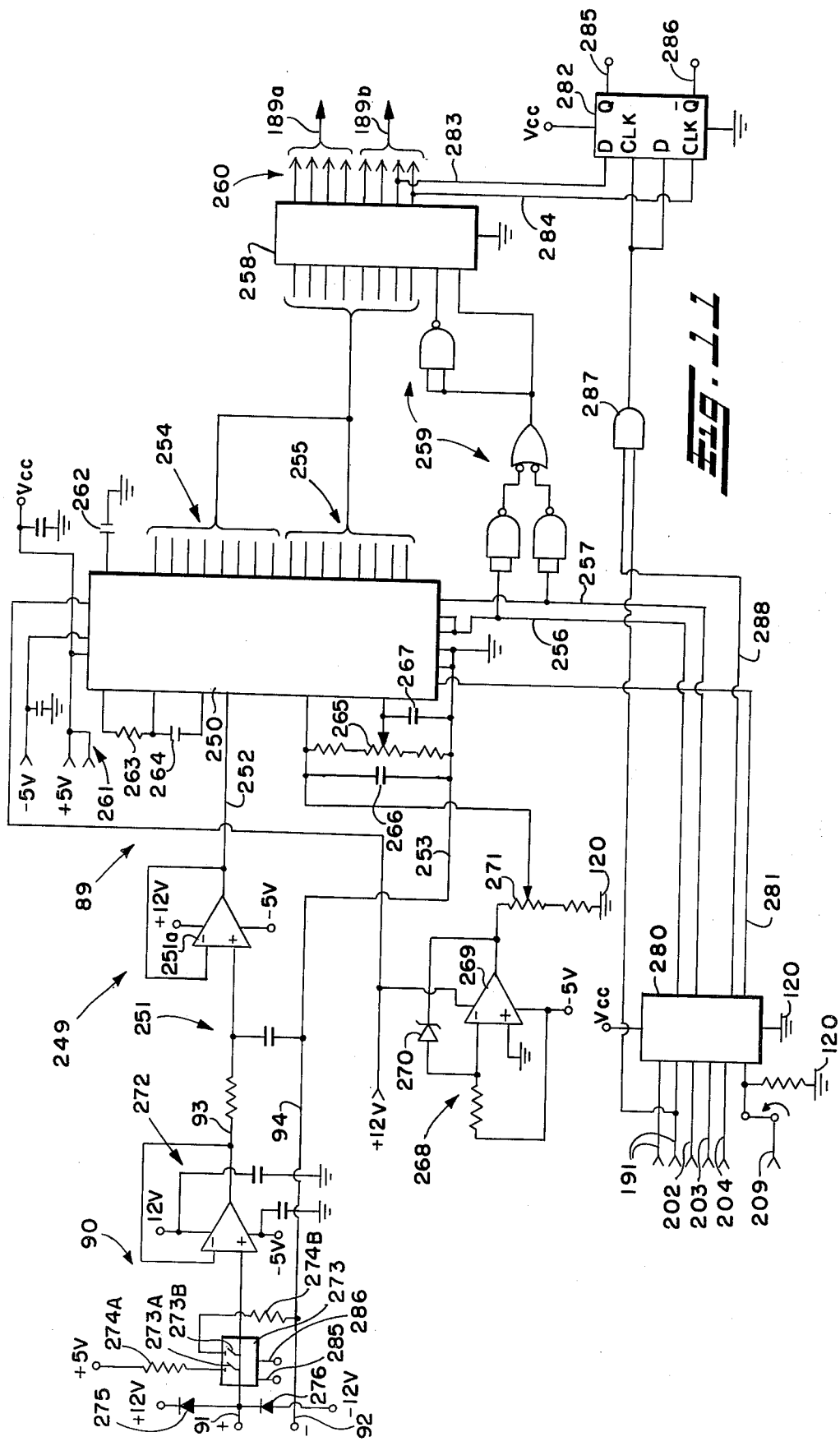
FIG. 11 is a schematic electrical circuit diagram of an analog to digital (A/D) converter circuit.

Input/output (I/O) port select signals are produced on lines 202, 203, 204 to indicate which I/O port is selected at any time. Lines 202-204 are connected to a three of eight decoder 205 which produces a high signal on line 206 when an I/O port is to be enabled. The signal on line 206 is delivered to the latch 190 as a chip select signal for the same. I/O port select lines 207 may be selectively enabled by the latch 190 to select respective I/O ports, as desired, according to information received from the data bus 189a, 189b; in the preferred embodiment primarily only lines 208, 209 will be used. A high signal on line 208 enables the tape drive 59 (FIG. 12) and the KDU 6 (FIG. 13) and a high signal on line 209 enables the A/D converter 89 (FIG. 11). Line 214 from the latch 190 is connected by an inverting amplifier 215 to a horn 215a for energizing the same when a malfunction is detected by the CPU 170 so the operator can take remedial action. The horn 215a also may be used to provide a programmable signal to indicate that a special measurement or entry should be made at that location.

A logic circuit 216, which includes a pair of OR gates 217, 218 connected to the respective lines 202-204 from the CPU 170 and a pair of NAND gates 219, 220, the latter being connected by line 221 to receive the memory read signal on line 200, control operation of the bus drive circuits 188a, 188 b. The purpose of the logic circuit 216 is to enable operation of the data bus in a tri-state mode, which is conventional, to prevent noise on the data bus 96 from the CPU 170 from passing downstream to the data bus lines 189a, 189b.

Operation of the CPU 170 and associated circuitry 171 will be described in further detail below in connection with the circuits illustrated in FIGS. 11-13 and the program flow chart information presented in the subsequent figures.

Measuring circuitry 249 for measuring the pipe-to-soil potential difference includes the A/D converter 89 shown in FIG. 11. The A/D converter 89 employs an A/D converter integrated circuit 250, such as an Analog Devices AD7550, which converts the analog signal input thereto through a conventional low pass filter 251 and amplifier 251a on lines 252, 253 to "potential indicating" digital data representing the magnitude of such analog signal. The circuit 250 is a quad-slope integrator with multiplexed output buses 254, 255 on which such digital data is delivered. Bus 254 is selected when a high signal is provided at multiplex control line 256 to produce such digital data; similarly digital data is produced on bus 255 when a high signal is provided at multiplex control line 257. The multiplexed output buses 254, 255 are coupled to an eight bit unidirectional buffer circuit 258, which is energized by NAND and NOR logic gates 259 each time one of the multiplexed control lines 256, 257 goes high. The output lines 260 from the buffer 258 are coupled to the data bus 189a, 189b to permit reading of the potential indicating digital data by the CPU 170 particularly for subsequent storage on the cassette, not shown, in the tape drive 59.

Electrical power is supplied to the circuit 250 at terminals 261, as shown. A capacitor coupling 262 to ground 120 is provided for the clock input of the circuit 250, and a resistor 263 and capacitor 264 integrator circuit is connected to respective terminals of the A/D converter circuit 250. Calibration for the circuit 250 is provided by a resistance divider circuit including a potentiometer 265 and a pair of capacitors 266, 267. A reference voltage for the circuit 250 is provided by a conventional reference voltage generator 268, which includes an operational amplifier 269, zener diode 270, and adjustable potentiometer 271.

The measuring circuit 249 also includes a multiplexed variable input impedance circuit 90 between lines 91, 92, on which the pipe to soil (electrolyte) signals are received from cable 51, and lines 93, 94 at the filtered input to the A/D converter 89. The input impedance circuit 90 includes a high impedance amplifier circuit 272 having, for example, an input impedance (R$_A$) of about 1×10$^{12}$ ohms, a multiplexer switch 273 including switches 273A, 273B, a fixed impedance 274A having a resistance (R$_B$) of, for example, about 22×10$^6$ ohms, and a fixed impedance 274B having a resistance (R$_C$) of, for example, 10×10$^6$ ohms. Diodes 276, 277 provide overvoltage protection. The multiplexing circuitry operates to test for a broken wire or lead connection to the test station or a high impedance reference electrode contact. Three different potentials can be recorded with this switch arrangement.

1. E$_1$—Normal potential, switches 273A and 273B open;
2. E$_2$—Switch 273B closed, switch 273A open;
3. E$_3$—Switch 273A closed, switch 273B open.

The multiplexer 273, such as an RCA 4052, is used as an analog switch. With such multiplexer switches open, the impedance of the circuit 90 will be at maximum value, i.e. that of the amplifier 272; with only the multiplexer switch 273A closed the impedance of circuit 90 approximately equals that of the resistor 274A, and with only the multiplexer switch 273B closed the impedance of the circuit 90 will be approximately equal to that of the resistor 274B.

In operation of the measuring circuit 249 the potential difference measurement of the signal across lines 91, 92 is made at least twice at each test location, e.g. each time a measuring interval control signal is produced by the distance measuring circuit 40. One such measurement of potential (E$_1$) is made with switches of multiplexer 273 open and the other potential (E$_2$) with only the multiplexer switch 273B closed; if the difference between the two measured potentials is less than or equal to a predetermined magnitude, say 5 millivolts, then the contact resistance between the reference electrode 63 or 64 and the earth electrolyte is assumed to be negligible and the first potential measurement E$_1$ is considered to be the true potential E$_T$, which will be recorded. However, if the magnitude of the difference between E$_1$ and E$_2$ exceeds the predetermined magnitude, then a third measurement of potential E$_3$ is made with only multiplexer switch 273A closed. If the magnitude of the latter potential E$_3$ exceeds a further predetermined magnitude, say 3.5 volts, then it is assumed that the connection between the DMU 3 and the test lead 12 is interrupted, e.g. due to a break in wire 11; the operator is then automatically signalled of the fault by sounding an alarm, e.g. horn 215a, and displaying an appropriate fault code on the display 7. However, if the latter potential E$_3$ is less than such further predetermined magnitude, it is assumed that there is a high impedance reference electrode to earth contact and the true potential E$_T$ then is calculated according to the equation 1 below:

$$E_T = \frac{E_1 E_2 \left( \frac{R_A}{R_C} - 1 \right)}{\frac{R_A}{R_C}(E_2) - E_1}$$

Such operation will enable the obtaining of substantially true potential (E$_T$) measurements without regard for changes in contact resistance between the respective electrodes 63, 64 and the soil (electrolyte). The true potential (E$_T$) is stored on the cassette and displayed on the display 7 by the CPU 170.

The A/D converter 89 also includes a three of eight decoder 280, such as an RCA integrated circuit Model CDP1853. The decoder 280 is connected to lines 191 and 202-204 of the CPU 170 and to line 209 of the latch 190. The decoder 280 controls starting of integration by the A/D converter 250 by providing a start signal on line 281 and also selects the input/output ports or buses 254 or 255 of the A/D converter circuit 250. For example, a high signal on line 209 is operative to enable the decoder 280 and, accordingly, the A/D converter circuit 250, and a high signal on line 281 causes the converter 250 to begin integrating the signal on line 252 in the RC integrator of resistor 263 and capacitor 264 according to typical quad-slope operation. The circuit 250 converts the potential difference analog signal on line 252 to digital information in the form of a pair of eight bit bytes, each byte containing, for example, two four bit binary coded decimal words. The higher order byte is capable of delivery to bus 254 and the lower order byte is capable of delivery to the bus 255 under control of the decoder 280 which controls the multiplex control lines 256, 257 in response to signals on lines 191, 202-204, and 209 from CPU 170 and latch 190.

The decoder 280 also controls a dual D-type flip-flop 282, such as an RCA CD4013, which is used to latch data from two of the data bus 189b lines 283, 284 at the output of buffer 258 to enable (close) or to disable (open) the analog switches of multiplexer 273 via lines 285, 286. An AND gate 287 is connected to one of timing lines 191 and to output line 288 from decoder 280 to receive periodic enabling signals therefrom to strobe data from lines 283, 284 into the latch 282 thereby selectively to open and to close the switch connections of multiplexer 273.

Figure 12:
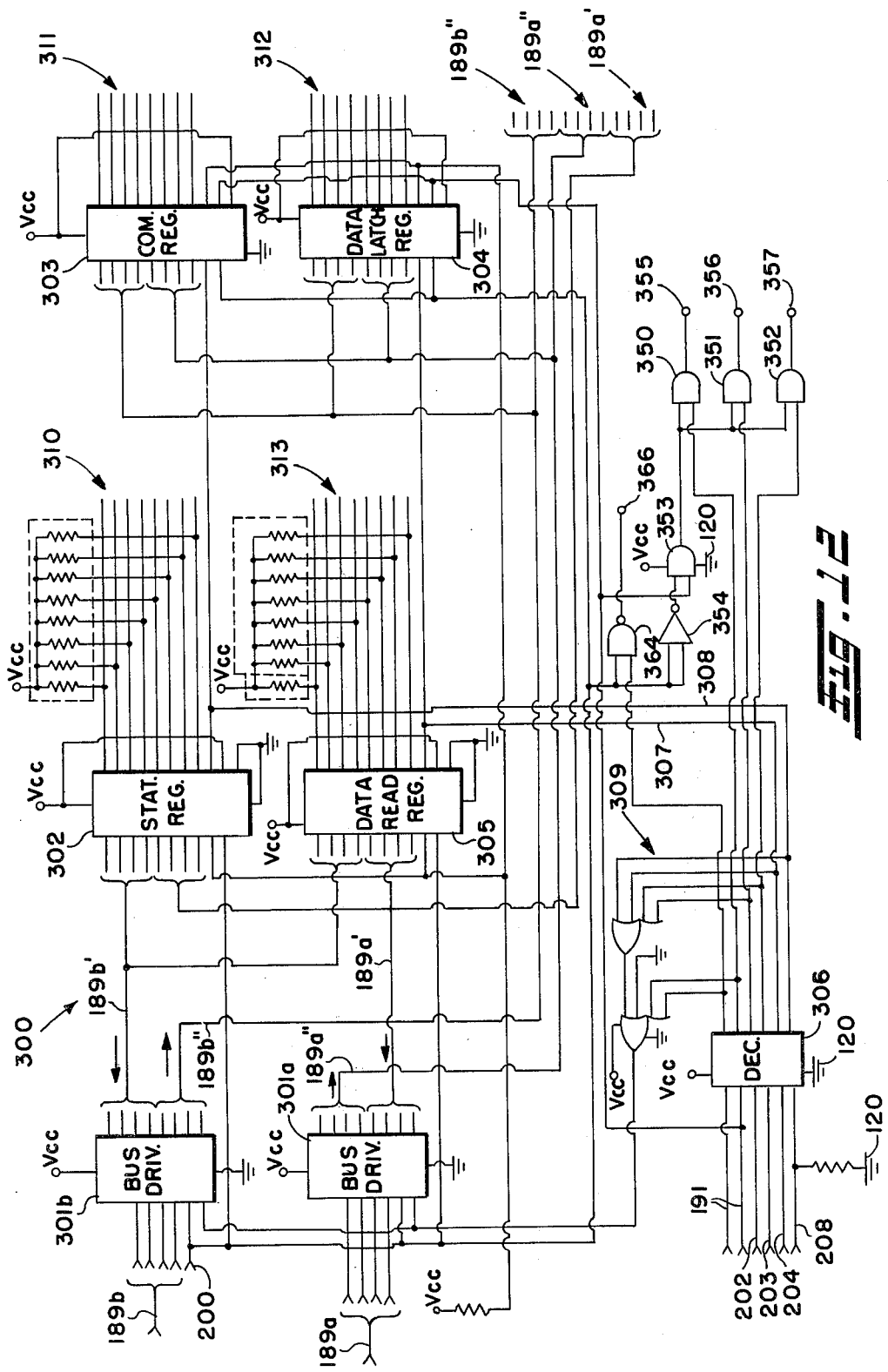
FIG. 12 is a schematic electric circuit diagram of an interface circuit for controlling a tape drive.

Referring to FIG. 12, now, the cassette tape drive interface circuit 300 is illustrated. It is the purpose of circuit 300 to interface with the tape drive 59, which includes an internal electronics control package furnished by the manufacturer Memodyne, to control the tape drive and to read and to write data with respect thereto. The cassette interface circuit 300 includes a pair of bus driver circuits 301a, 301b, such as RCA integrated circuits Nos. CDP1857D coupled, respectively, to the bidirectional data bus lines 189a, 189b. The bus driver circuits 301a, 301b also are connected by line 200 to the memory read terminal of the CPU 170 (FIG. 10). The bus driver 301a divides the data bus lines 189a to a duplicate pair of single direction buses 189a' and 189a" as respective data input (receiving) and data output bus lines, as represented by arrows in FIG. 12. Similarly, the bus driver 301b divides the data bus line 189b to a duplicate pair of unidirectional input and output bus lines at 189b' and 189b". The bus drivers 301a, 301b are connected, as illustrated, to four eight bit data latch circuits 302-305. An input/output port decoder circuit 306 is connected to lines 191 and 202-204. The decoder 306 in association with one of the timing lines 191 and the memory read line 200 determines which of the latch circuits 302-305 is to be operated at any given time by connections to lines 307, 308. The memory read signal on line 200 is delivered to the chip select ports of the latch circuits 302-305. An OR gate logic circuit 309 couples the various output lines from the decoder 306 to the bus drivers 301a, 301b to operate the same whenever high signals are on the respective input lines to the OR gates 309. The output lines 310 from the cassette status register, latch circuit 302, are connected to respective terminals of the tape drive 59 to test the latter.

Depending on the signals received on the lines 310 from the tape drive, the latch 302 effectively tests to learn whether the cassette is in place, the tape in the cassette is at the beginning or end of the clear leader thereof, the tape head is engaged, the cassette is write protected, and the cassette is busy or not, e.g. a read, write, rewind, or loading forward process is occurring. The cassette command register, latch circuit 303, is connected by lines 311 to the tape drive to control operation thereof, for example, to rewind, reverse, write, read, back space, stop, start, and load forward. The data latch, latch circuit 304, is connected by lines 312 to the tape drive to deliver data for writing onto the cassette, and to that end the eight lines 312 provide respective bytes of information for recording on the tape of the cassette. The data read latch, latch circuit 305, is connected by lines 313 to the tape drive to read the data from the cassette after it has been written onto the cassette for verification purposes and display in the display 7. Each of the latch circuits 302–305 may be an RCA integrated circuit No. CDP1852D.

Figure 13:
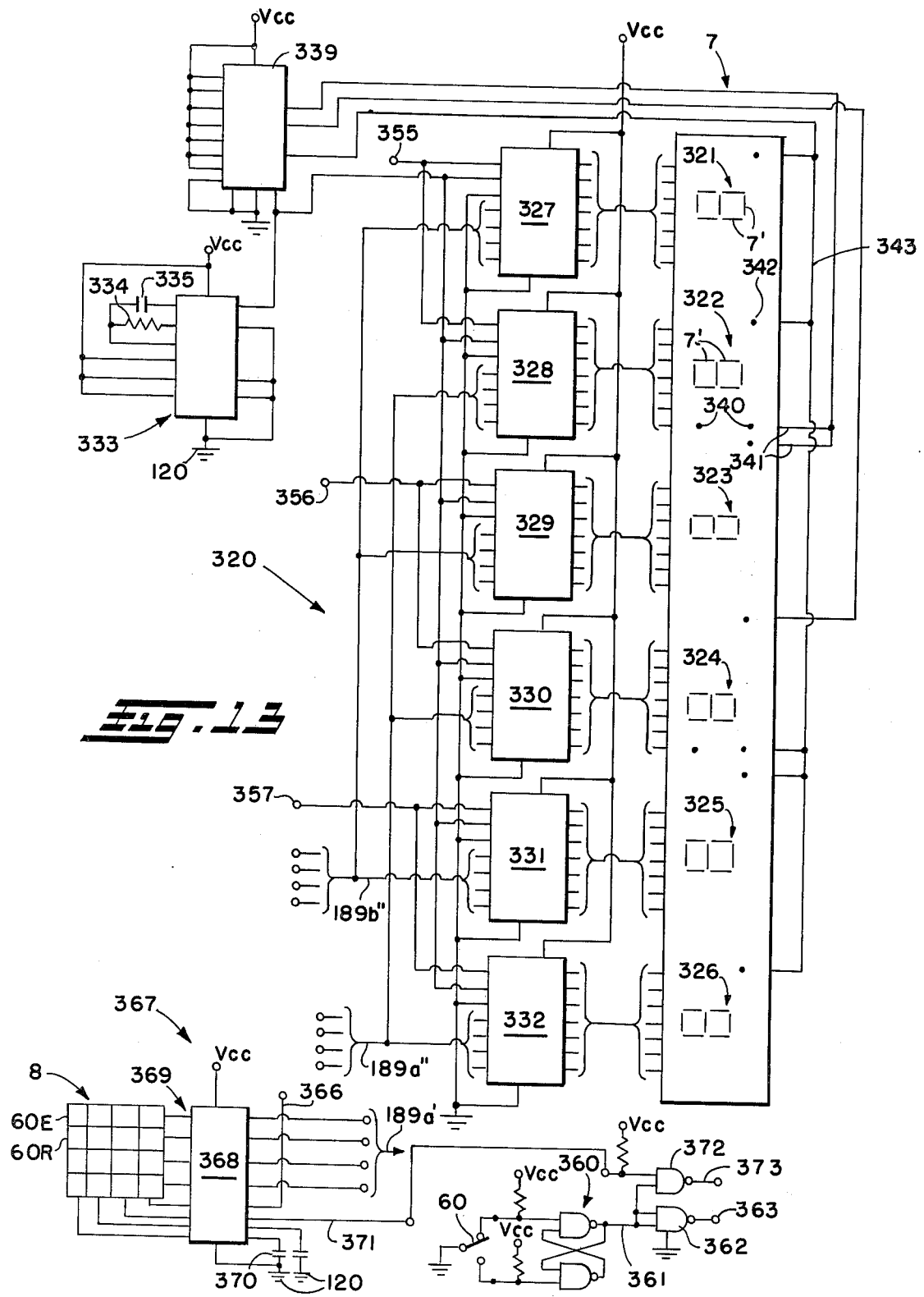
FIG. 13 is a schematic electric circuit diagram of the KDU circuitry.

The data bus lines 189*a''* and 189*b''* from the bus drivers 301*a*, 301*b*, respectively, are coupled to the display circuitry 320 to effect control of energization of the plural liquid crystal display elements 7' making up respective digits 321–326 of the display 7, as is shown in FIG. 13. The first two digits 321, 322 preferably are data control digits (DCD) that indicate certain status or operation information about the system 1, such as whether the system is operating in an initialization, feature data entry, or potential measuring modes, an error or fault condition has occurred, etc.; and the latter four digits 323–326 are data display digits (DDD) that display, for example, electrical potential difference that is being measured by the system 1, feature information, etc. Each of the bus lines 189*a''* and 189*b''* is connected to three respective integrated circuit binary coded decimal seven segment decoder and display driver latch circuits 327–332, such as RCA integrated circuits No. CD4056. The drivers 327–332 are coupled by respective bus type connections, as is illustrated in FIG. 13, to effect energization of respective liquid crystal display elements 7' of the individual liquid crystal digits 321–326 to display certain alphanumeric data thereby. A square wave generator 333 including, for example, an RCA integrated circuit No. 4047 and a resistor 334 and capacitor 335 circuit, provides a square wave signal for conventional purposes to the drivers 327–332. Moreover, a four bit display driver 339, e.g. RCA 4054, is provided for blanking and energizing respective colons 340 via leads 341 and decimal points 342 by leads 344, as desired.

Three display driver enabling AND gates 350, 351, 352 are coupled to respective output lines from the decoder 306 (FIG. 12) and to an AND gate 353 and inverting amplifier 354. When there is no memory read signal on the line 200 from the CPU 170 the AND gate 353 will enable the AND gates 350–352. Then, according to respective output signals from the decoder 306, respective AND gates 350–352 will produce high signals on lines 355–357, respectively, to enable respective driver circuits 327–332 to energize respective display digits 321–326 (FIG. 13).

The keyboard enable and disable switch 60 is connected to an enabling latch circuit 360. When the switch 60 is in its keyboard enabling position, a signal produced on line 361 causes the NAND gate 362 to produce on line 363 a signal that is coupled directly to the CPU 170 (FIG. 10) for causing the CPU to enable the keyboard 8 and to read the same. On the other hand, when the switch 60 is in its disabling position, the output signal from the latch 360 and NAND gate 362 will prevent the CPU 170 from reading the keyboard, thereby effectively electronically disabling the latter.

A NAND gate 364 receives inputs from the memory read line 200 and line 365 from the decoder circuit 306 (FIG. 12) when the CPU 170 has received a signal on line 363 indicating that the keyboard 8 is enabled by switch 60; when both inputs to the NAND gate 364 are logic one, an electronic enabling signal is delivered via line 366 to the keyboard circuitry 367 (FIG. 13). The electronic enabling signal on line 366 enables a keyboard decoder circuit 368, such as a National 74C922, to convert information received on bus lines 369 from respective keys of the keyboard 8 to binary coded decimal information on data bus lines 189*a'*. A capacitor 370 provides debouncing function to eliminate transient signals produced on lines 369 upon closure of respective contacts as keys of the keyboard 8 are pressed.

A keyboard data available line 371 provides a low signal from the decoder 368 when any key of the keyboard 8 has been pressed to operate through a NAND gate 372 which provides information to the CPU 170 (FIG. 10) indicating that a key has been pressed so that the CPU will read the information from such key. More particularly, line 373 from the NAND gate 372 is connected to a correspondingly numbered line directly to the CPU 170, as is seen in FIG. 10. When such keyboard data is to be read, the data is provided via data bus 189*a'* (FIGS. 13 and 12) to bus driver 301*a* and from the latter to the data bus 189*a* from which it is read.

The preferred embodiment of the invention, including both the apparatus and the method of using the same to effect surveys has been described above. The following description will be directed to the flow charts of FIGS. 14–25, which present information concerning the best mode of operation of the apparatus 1 under control of the microcomputer 80 to carry out the method of the invention.

The flow charts of FIGS. 14–25 are subroutines called during operation of the main program flow chart shown in FIG. 8. It will be appreciated that the steps represented by the various blocks in the flow charts may be converted in conventional manner by a person having ordinary skill in the art to computer language and information that may be stored in the ROM 84 for controlling operation of the microcomputer 80 and the overall apparatus 1. Although not illustrated, it will be appreciated that various subroutines are entered or called and are returned from via typical enter or call and return routines that keep track of various conditions existing and program location when going to respective subroutines.

In the preferred embodiment the microprocessor 81 is an RCA CDP1802 with sixteen internal registers (scratch pad registers), and, accordingly, the flow charts and program described below are compiled for operation with such microprocessor. Of course, other types of microprocessors may be used with appropriate modifications being made in the flow charts and program.

During the initialize registers operation, block 103 of FIG. 8, the internal registers in the CPU 170 are initialized. For example, addresses for two stack pointers, namely a parameter stack pointer (PSP) and a program stack pointer (SP) are stored in respective internal registers 6 and 2 of the microprocessor 81, for example; the register (e.g. register 3) for containing the program counter (PC) is established, and the addresses for pointing to respective subroutines, including the "enter" routine and the "return" routine, are established.

When the system initialization subroutine (ISYS), block 104 (FIG. 8), is called, the flow chart follows FIG. 14. At block 400 I/O port 3 is selected causing a high signal on line 208 (FIG. 10) which enables the circuits associated directly with the tape drive 59, display 7 and keyboard 8 of FIGS. 12 and 13. At the same time a low signal an I/O port 2, i.e. line 209 (FIG. 10), maintains the A/D converter 89 disabled. Thereafter, the cassette command register 303 (FIG. 12) is initialized, block 401. This causes the cassette command register 303 to output an eight bit data word that, for example, includes a stop pulse to assure the cassette is stopped; a forward direction bit to assure the tape drive is ready for forward, not reverse, operation; a write bit, as opposed to a read bit; a now rewind bit; a not load forward bit; and a not start bit.

The cassette status is input, then, to status register 302, (FIG. 12), block 402, and that status is read by the CPU 170 to determine, by conventional bit comparison techniques, whether the cassette is in place and the tape head is loaded down, block 403. If the answer to the inquiry made at block 403 is affirmative, then a load forward command is output to the tape drive 59 via the command register 303, (FIG. 12) block 404. A load forward causes the tape drive to generate an inter-record gap on the magnetic cassette tape, which signifies the start of a survey. Data will then be recorded on the tape following such gap, and the tape drive now should be ready to record. The cassette status again is checked, block 405, by reading the status register 302, and the CPU 170 checks whether the load forward operation, which takes about one second, has been completed, block 406. If the answer to the inquiry in block 406 is negative, then the flow chart enters a loop via line 407 until the load forward operation has been completed. After completing the load forward operation, block 406, the flow chart of FIG. 14 returns via the return subroutine to the flow chart 100 in FIG. 8.

Still referring to FIG. 14, if the answer to the inquiry made at block 403 is negative, indicating that the cassette is not in place or the head is not loaded, then a cassette not ready (CNR) subroutine is called at block 410. The CNR subroutine illustrated in FIG. 15 is entered via the "enter" subroutine. A cassette control code, i.e. a specified data word, indicating that the tape drive 59 is not ready is loaded into the accumulator of the CPU 170 preferably by a load immediate instruction, block 411. Next, at blocks 412–414 it is intended to effect operation of the display 7 to display specified data, in this case a code "H1" with the first digit meaning that something is wrong with the system and the second indicating that the problem is at the tape drive 59.

Each internal register of the microprocessor 81 or CPU 170 is divided into two eight bit portions, such as registers 8.0 and 8.1, collectively referred to as register 8, and register 8.1 is loaded at block 412 with an eight bit data word, the data control bits (DCB), that will cause the data control digits (DCD) 321, 322 of the display 7 (FIG. 13) to display the code "H1". In particular, the four high order bits in the eight bit word stored in register 8.1, when appropriately decoded as binary coded decimal data, for example, will cause the display digit 321 (FIG. 13) to display the letter "H". Similarly, the lower four order bits in register 8.1 will control the display digit 322 (FIG. 13) to display "1".

Register 9 of the CPU 170 is used to store a sixteen bit data word, including four discrete four bit words, referred to below as the data display bits (DDG) used to control the data display digits 323–326 (FIG. 13). At block 413 register 9 is loaded with blanks such that the DDG will cause the data display digits 323–326 to be blanks. At block 414 the load display subroutine (LDDSP) is called, and is entered via the enter subroutine.

As the first step in the LDDSP subroutine illustrated in FIG. 16, in block 415 the parameter stack pointer (PSP) is set or selected, for example to be contained in register 6; the X register in the CPU 170, accordingly, is loaded with information designating register 6 as the PSP to which the CPU will refer for subsequent steps. The PSP points to the address of an empty memory word location in the RAM's 184, 185 (FIG. 10). Each RAM IC provides 4 bits of an 8 bit word at each RAM memory. When writing to RAM, information is, accordingly, written to both RAM IC's. At block 416 the DCB from register 8.1 is loaded into the accumulator of the CPU 170 as well as into the RAM memory location addressed by the PSP and is output to the latches 327, 328 which then energize the data control digits 321, 322 to display the code "H1". The CPU 170 automatically increments the PSP when the RAM memory location addressed by the PSP has been used; accordingly, at block 417 the PSP is decremented by one so that it will be seen that the memory word location addressed by the PSP is used only as a "dummy" location due to the particular requirements of the CPU 170. During such loading of the DCB into latches 327, 328, various I/O instructions to the decoder 306 (FIG. 12) will have operated respective NAND gates 350–352 selectively to enable the respective latches 327, 328, as illustrated.

Similarly, at block 418 the DDG from register 9.1 is loaded into the accumulator and into the RAM memory word location addressed by the PSP and is output to the latches 329, 330, as enabled or strobed to open by a signal from NAND gate 351, for controlling the data display digits 323, 324; in this case, such data display digits will be blanks. The PSP is decremented again at block 419 and a similar operation is carried out at block 420 to load the lower order byte of DDG from register 9.0 and to display the blanks commanded thereby at data display digits 325, 326, as commanded by latches 331, 332. The PSP is decremented again at block 421, and the flow chart returns via the return subroutine to block 422 of FIG. 15.

Figure 17B:
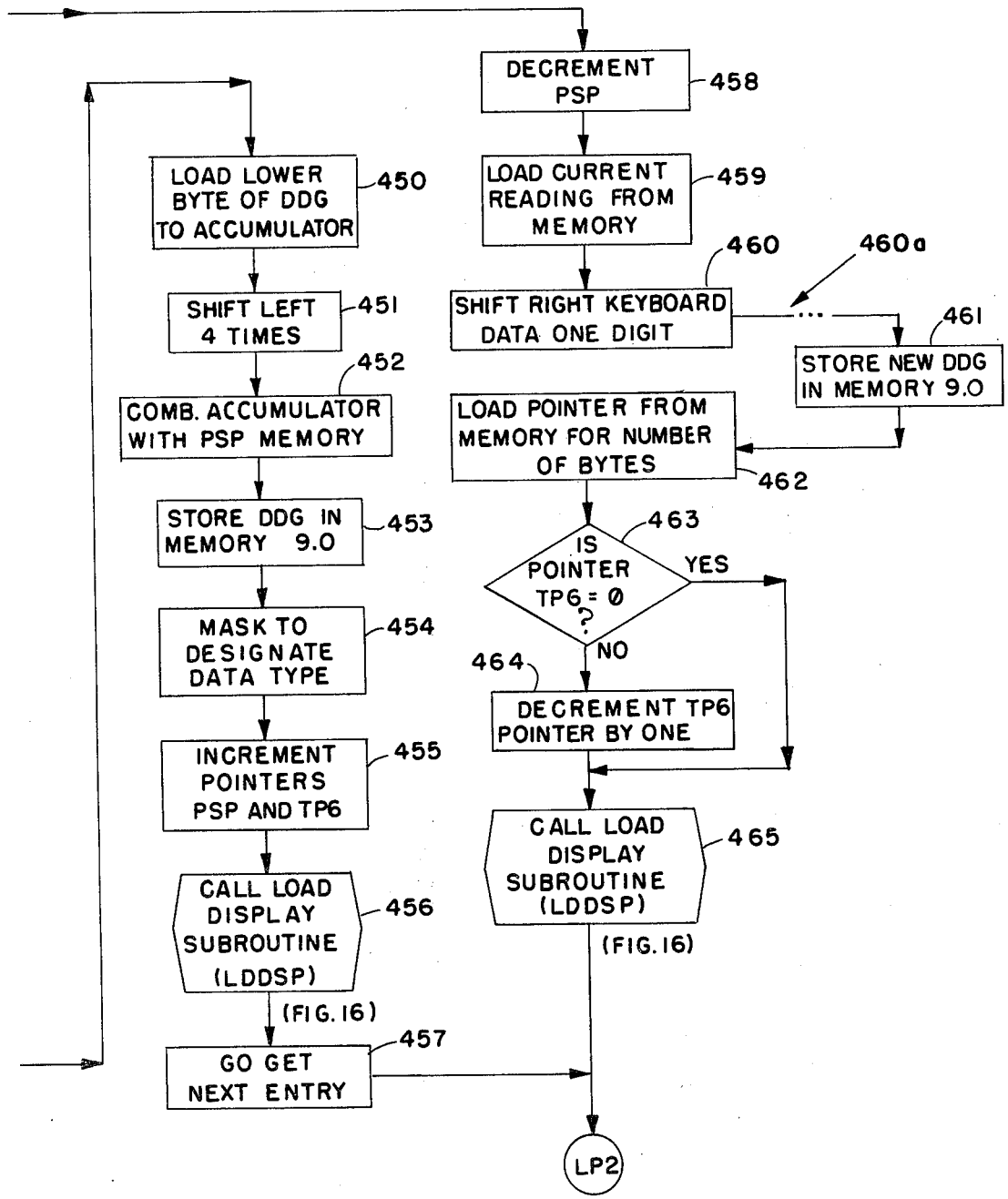

At block 422 an enter keyboard data (EKB) subroutine is called. The EKB subroutine is illustrated in FIGS. 17A and 17B. The primary purpose of entering the EKB subroutine at this time, realizing that entry was due to the cassette not being ready at block 410 of FIG. 14, is to cause the surveyor or operator of the apparatus 1 to acknowledge a realization that the cassette was not ready. Such acknowledgemement is obtained by the operator enabling the keyboard 8 via the switch 60 and pressing the enter key 60E (FIG. 13).

At block 423 of the EKB subroutine (FIG. 17A) an inquiry is made to determine whether the keyboard 8 is enabled by the switch 60, in which case a signal is delivered to input line or terminal 363 of the CPU 170. If the keyboard is not enabled, the flow chart follows a loop via line 424 waiting for such enabling.

When the keyboard 8 is enabled, I/O port 3 is selected, block 425, whereupon the CPU places a high signal on line 208 of the output latch circuit 190, thereby enabling the cassette interface circuit 300, display circuitry 320, and keyboard circuitry 367. The measuring circuitry 249 is disabled then due to a low signal on line 209, I/O port 2. The signals on I/O port select lines 208, 209 usually will be complementary.

The PSP is initialized, block 426, to select CPU internal register 6 and to place into such register the address of a RAM memory word location at which data can be stored on the parameter stack. Thereafter register X is set to tell the CPU 170 which internal register holds the PSP, block 427. An inquiry is made to see whether the keyboard 8 has been enabled, block 428, by the CPU 170 checking line 373 again. If the keyboard is not enabled, then blanks are loaded into the DDG register 9, block 429, and at block 430 the LDDSP subroutine is called (from FIG. 16) to display blanks at display digits 323–326.

However, if the keyboard 8 is enabled at block 428, an inquiry is made, block 431, to see if any keyboard data is available, i.e. if any key is pressed. For example, line 373 (FIG. 13) will go high when any keyboard key is pressed to indicate directly to the CPU 170 that the keyboard should be read. The keyboard data then is read from the bus 189a'. If there is no data available, i.e. a key is not pressed, the flow chart follows a loop via line 432 until a key is pressed or the keyboard is disabled; in the latter case the flow chart follows the blocks 429 and 430, as above.

When keyboard data is available, block 431, it is input via the data bus 189a', block 433, to the CPU 170. Since there are only sixteen keys on the keyboard 8, each may be identified by only four bits, which are applied to the four data bus lines 189a'. Such four bits are loaded, for example, into the first four or four low order bits of the CPU accumulator, and at block 434 the upper four bits of the accumulator are masked out. At block 435 the four bit data word identifying the keyboard data, i.e. the just pressed key, is stored on the parameter stack, as addressed by the PSP. A time delay is provided at block 436 and loop 437 until the key has been released. Thereafter, an inquiry is made at block 438 to see whether the pressed key was the data enter key 60E. Assuming that the enter key 60E was pressed to indicate the operator's acknowledgement that a fault had been detected, for example the cassette not being ready, it also being assumed that the fault has now been corrected, the flow chart follows line 439 to blocks 429, 430 and ultimately to block 402 (FIG. 14) to continue in a loop until the cassette is in place and the head is loaded, as inquired at block 403 of FIG. 14.

The steps identified at 440–457 coordinate the entry of data via the keyboard 8 and display of the same at respective data display digits 323–326. When a data key is pressed, the numerical value of that key is to be displayed at the lowest order data display digit, such as digit 326; and when the next data key is pressed, the first data value will be shifted one place to the left for display at the next higher order data display digit, such as at digit 325, and the newly pressed data value will be displayed in the lowest order data display digit 326; and so on. When all four data display digits 323–326 are occupied, pressing of another data key on the keyboard 8 will cause the data value in the highest order display digit to be shifted off the display 7, as its place is occupied by the next lower order bit; but the data value shifted off the display will still be stored in memory for recall, if desired.

Referring to block 440 of FIG. 17A, an inquiry is made to see whether the pressed key is the data rub-out or erase key 60R; if not, the PSP is incremented at block 441 to address an empty RAM memory word location of the parameter stack. The higher order 8 bit byte of data display bits (DDG) from register 9.1 is loaded into the CPU accumulator, block 442. That byte, the four higher and four lower order bits of which respectively control the highest and next highest order display digits 323, 324, is shifted left four times, block 443, to destroy the highest order data value, although its value is still stored at a specified location in RAM 85. The shifted data then is stored in the parameter stack, block 444; the four bits of such stored word represent the value of the highest order data display digit 323. Thereafter, the lower byte of DDG data from CPU register 9.0 is loaded into the accumulator, block 445, and is shifted to the right four times, block 446, to isolate in the lower four order bit positions the value of the next highest order of data display digit 324. The first and second digits just obtained are combined, block 456, by combining the value then in the accumulator with that in the RAM memory word location addressed by the PSP. The new data word thus obtained is stored in CPU internal register 9.1 (the high order DDG register), block 448, with the upper four bits of such word controlling the data display digit 323 and the lower four bits controlling the data display digit 324.

Thereafter, the PSP is decremented, block 449, to point to the RAM memory word location at which the data value representing the just pressed key is stored. The lower eight bit byte of display data (DDG) from register 9.0 is loaded into the accumulator, block 450, is shifted four times to the left, block 451, and is combined, block 452, with the key data value, i.e. the data value of the just pressed key, from the parameter stack to form an eight bit display word representing the lower values of the lower two order data display digits 325, 326 to be displayed by the display 7. The new display data word (DDG), then, is stored in CPU internal register 9.0, block 453. Masking is then provided in conventional manner, block 454, to designate that the type of data stored in register 9.0 is a command or feature code entered from the keyboard 8 rather than a potential difference value.

At block 455 the PSP is incremented to point to an empty RAM memory word location containing the parameter stack and another pointer TP6, which is a word pointer indicating the number of four bit codes that have been written into memory due to pressing of sequential keys from the keyboard 8, also is incremented. The pointer TP6 may be contained, for example, in CPU register 15. At block 456 the LDDSP subroutine, FIG. 16, is called to effect display of the DDG information then contained in CPU register 9. Upon completion of the LDDSP subroutine, the flow chart follows block 457 and loop LP2 back to block 427 of FIG. 17A.

When no more data is to be entered from the keyboard 8, the keyboard is disabled by switch 60. The flow chart then returns, as aforesaid, via blocks 428–430 to block 402 of FIG. 14 and enters either the aforedescribed loop via the negative of block 403 or proceeds via the affirmative of block 403 ultimately to block 105 of the flow chart of FIG. 8.

The steps denoted in blocks 458-465 (FIG. 17B) are intended to eliminate from the DDG information stored in CPU internal register 9, which controls the data display digits 323-326, the value of the lowest order data display digit. Thus, upon pressing the rub-out key 60R, the last data value entered by a key from the keyboard 8 is erased, and the remaining data display digits of the display 7 are shifted one place to the right, either leaving a blank in the highest order data display digit 323 or the data value that had been shifted off the display but still was stored in memory.

Thus, in FIG. 17B, if the key pressed is the rub-out key 60R, the PSP is decremented, block 458, to point to the last word entered in the parameter stack. The current reading or output of the display 7, which is stored in CPU register 9, is loaded into the CPU accumulator, block 459. Such data in the accumulator is shifted to the right by one complete digit, i.e. by four bits to eliminate the four bits just previously controlling the data display digit 326, block 460. Moreover, the steps described above with respect, for example, to blocks 441-454 may be repeated in conventional manner to obtain effectively a reverse operation, as represented by the break 460a in the line of the flow chart, ultimately to obtain a new DDG data word for storage in CPU register 9, block 461. The next step is to load into the accumulator the value of the pointer TP6 from register 15 for the number of four bit words entered from the keyboard and stored in memory, block 462. An inquiry is made at block 463 to see whether the pointer TP6 is zero; if not, the pointer TP6 is decremented by one, block 464, and the LDDSP, FIG. 16, is called at block 465 to display on the data display digits 323-326 the new DDG information in CPU register 9. After the LDDSP subroutine has been completed, the flow chart returns via loop LP2 to proceed according to the steps described above commencing, for example, at block 427 in FIG. 17A. However, if the pointer TP6 is found to be zero at block 463, indicating that no DDG data should be in register 9, then line 466 is followed bypassing the decrementing step of block 464 ultimately calling on the LDDSP subroutine at block 465, as aforesaid, to display blanks at display digits 323-326.

The survey initialization subroutine (ISUR), block 105 in FIG. 8, now is called to enter numerical codes in the apparatus 1 for storage on the cassette tape. These codes may be read out in the future by a computer when the information on the tape is analyzed. The codes may be used to identify, for example, the company for which the survey is being made, the pipeline being surveyed, the particular segment of the pipeline being surveyed, the direction of the survey, e.g. against or with the flow of the pipeline product, the month, day, and year of the survey, and the crew making the survey.

Referring to FIG. 18, the ISUR subroutine is presented. At block 469 the DCB register 8 is loaded with the DCB data word requiring the display control digits 321, 322 (FIG. 13) to display "LO", which indicates that the apparatus is ready to accept information identifying the name of the company for which the survey is to be made. At block 470 the DDG register 9 is loaded with information that will cause the data display digits 323-326 to display blanks. At block 471 the LDDSP subroutine (FIG. 16) is called to display "LO" in the data control digits 321, 322 and blanks at the data display digits.

At block 472 data type masks are set; a register, say register 14, at which an address or pointer TP5 will be found, is designated to address a RAM memory word location containing the data masks. The purpose of such masks is to indicate that the immediately following data that will be stored on the cassette tape is initial information about the survey.

The enter keyboard data subroutine (EKB) is called at block 473, then, to permit the operator to enter into memory the information which identifies the company for which the survey is being made. After the operator has entered on the keyboard 8 appropriate code for designating such company, the operator would press the enter key 60E in order to return from block 438 in FIG. 17A of the EKB subroutine. Thereafter, at block 474 the cassette write subroutine (CWRT) is called to operate the tape drive 59 in an incremental manner to store on the tape information just entered by the operator.

Figure 19:
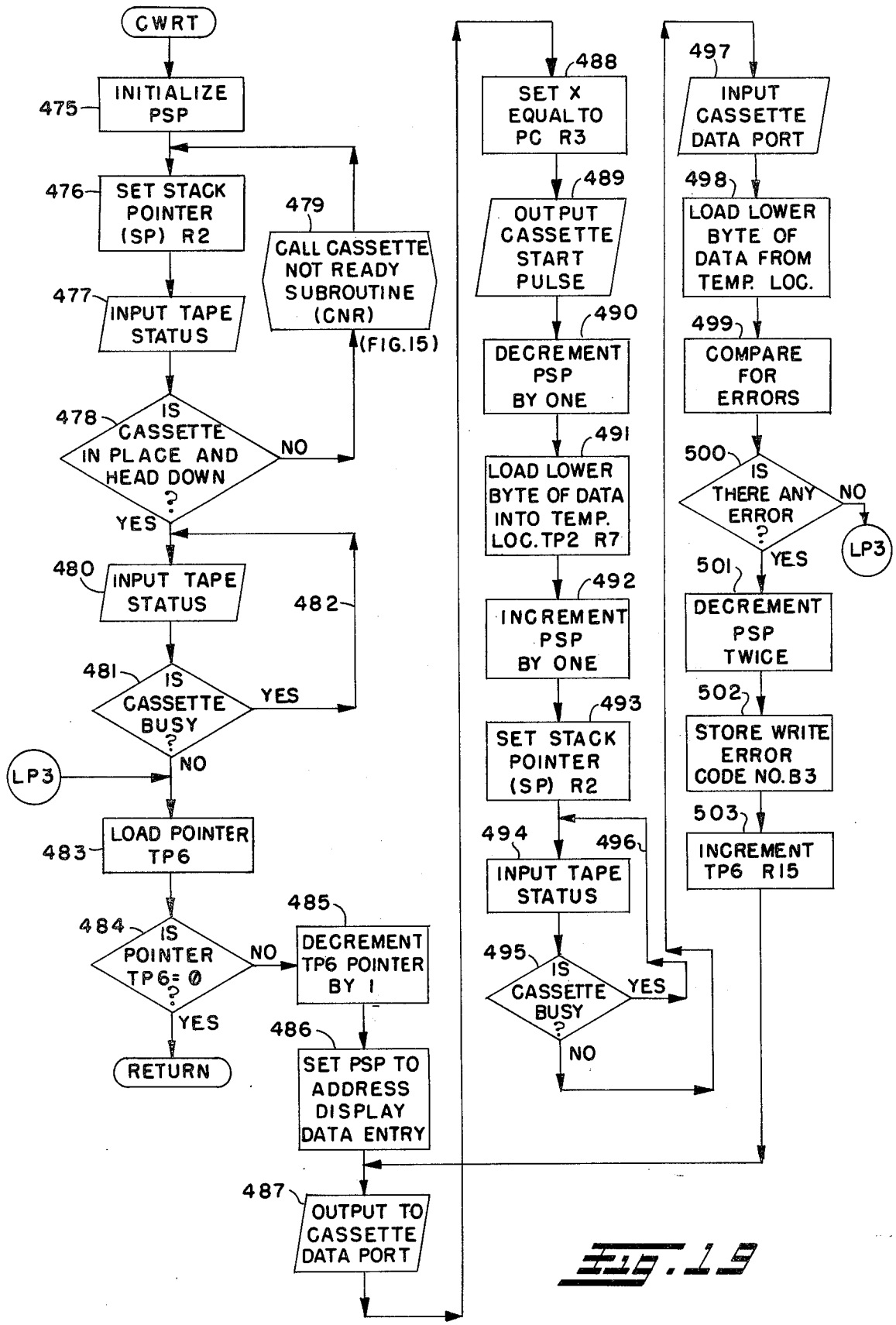

Referring now to FIG. 19, the CWRT subroutine is illustrated. At block 475 the parameter stack pointer (PSP) is initialized to point to a location in RAM which is at the top of the parameter stack in which the data was entered, for example, during the EKB subroutine. The stack pointer (SP) is set at block 476 to tell the CPU 170 in which register, namely register 2, the stack pointer is located. The stack pointer identifies an address in RAM at which data will be stored when it is received on the data bus 189. The status of the cassette tape drive is input at block 477 to the address in RAM designated by the stack pointer, block 477, as described with reference to block 402 (FIG. 14) above. An inquiry is made to sense whether the cassette is in place and the head is down at block 478; if the response is negative, then the CNR subroutine, FIG. 15, is called at block 479. If the answer at block 478 is affirmative, then the tape status again is input at block 480 by strobing cassette status information from lines 310 into the status register 302 (FIG. 12). At block 481 an inquiry is made to sense whether the cassette tape drive is busy. If the cassette is busy, a loop is entered via line 482 until the cassette no longer is busy. When the cassette is no longer busy, at block 483 the accumulator is loaded with the value of the pointer TP6 from register 15 to indicate the number of words of data left to write onto the tape.

Assuming that the pointer TP6 is not zero, at block 484, then that pointer is decremented by one at block 485. At block 486 the PSP is set again to tell the CPU at which register, namely register 6, the parameter stack is located. At block 487 the information, namely that just entered from the keyboard 8 during the EKB subroutine, stored at the memory location in RAM addressed by the PSP is output to the cassette data latch 304 (FIG. 12) via the buses 189a, 189b and 189a'' and 189b'' to make that data available to the cassette tape drive when requested by the latter according to conventional internal control circuitry thereof furnished with the tape drive by Memodyne. After such data is output to the cassette data latch, the PSP is automatically incremented by one at block 487 ordinarily to point to the next location in the parameter stack. This incrementing is an automatic operation of the RCA CDP1802 microprocessor.

Next the data in the data latch 304 is to be recorded by the tape drive 59 on the cassette tape by an "output immediate" type of instruction, whereby a word is taken from memory and is output to an output port. Accordingly, at block 488 the X register of the CPU 170 is set to a value that designates the program counter register 3. The X register is the memory address register of the CPU 170, and, therefore, by setting the same to address the program counter register, the CPU is effectively set up for an output immediate type of function. Thereafter, at the cassette command register data latch 303 a brief start pulse is delivered on one of the output lines thereof, block 489, to start the tape drive 59. The eight bits of data from the data latch 304 then will be serially recorded on the cassette tape.

To assure validity of the data recorded on the cassette tape, an error checking operation occurs according to the steps 490-503. The PSP is decremented by one, block 490, to address the location in RAM from which the data just written on the cassette tape was derived. At block 491 the byte of data from such addressed RAM location is loaded into a temporary location in the CPU 170, such as in pointer TP2, which is the lower byte of internal register 7 (7.0). The PSP is incremented by one, block 492, to point to the next data word in the parameter stack that should be the next word to be written on the cassette tape. At block 493 the stack pointer (SP) is set to cause the CPU to look to its internal register 2 for the next RAM address at which data will be read or written. At block 494 the tape drive status is input to the RAM location addressed by the stack pointer. An inquiry is made in conventional bit comparison technique, block 495, to detect whether the casette is busy or not; if the cassette is busy, a time delay waiting loop is entered at line 496. If the cassette is not busy, the data received on lines 313 from the tape drive, which indicates the data just written on the cassette tape, is latched into the read or verification data latch 305 and is delivered via bus lines 189a' and 189b' to the location in RAM addressed by the SP. The accumulator, then, is loaded at block 498 with the lower byte of data from the temporary location of pointer TP2 and at block 499 a comparison is made between the accumulator data and that stored in the RAM location addressed by the SP. At block 500 an inquiry is made whether an error exists; if there is no error, the flow chart follows loop LP3 to block 483 so as to write the next word from the parameter stack onto the cassette tape or, if the pointer TP6 is zero at block 484, to return back to the ISUR subroutine of FIG. 18.

However, if there is an error found at blocks 499 and 500, then at block 501 the PSP is decremented so as to point to a location in the parameter stack that is an unused location or in which it is no longer necessary to retain data. At block 502 a "write error" code, e.g. "B3", is stored at such location addressed by the PSP. The write error code is provided for ultimate storage on the cassette tape so that upon play-out, for example, during analysis by a computer, such computer will receive such code as an indication that the immediately preceding data may contain an error. At block 503, then, the pointer TP6, register 15, is incremented by one to indicate that the number of words stored in the parameter stack equals the error code plus the data word in which an error was just detected, plus the number of remaining data words in the parameter stack still to be written onto the cassette tape. Thereafter, the CWRT subroutine follows through blocks 487 et al to block 500; if there has been no error encountered in the recording of the write error code onto the cassette tape, as inquired at block 500, then loop LP3 is followed as aforesaid to complete the writing of information onto the cassette tape. Thus, any time an error is found at block 500, two extra words will be written onto the cassette tape, namely the write error code and the immediately preceding word in which an error had been found at the time it was to have been written onto the cassette tape.

When the pointer TP6 is zero, block 484, the flow chart flows to block 510 (FIG. 18) where an inquiry is made to determine whether the DCB value has reached 7. Originally, the DCB value had been zero (block 469) with a prefix "L". If the DCB is not yet 7, the DCB is incremented by one in block 511, and the procedures designated in blocks 471-474 are repeated via loop line 512 until all the feature codes are entered and stored on the cassette tape.

When the inquiry made at block 510 is affirmative, the ISUR subroutine proceeds to block 513, whereupon the continuous potential mode subroutine (CPM) of FIG. 20 is called. The purpose of the CPM subroutine is to measure and to display the potential difference between the structure being surveyed and the electrolyte, such as soil contacted by the electrodes 4, to advise the operator that the system is working properly; however, until a further command is entered by the operator, no measurement data is stored in the cassette tape.

Figure 21:
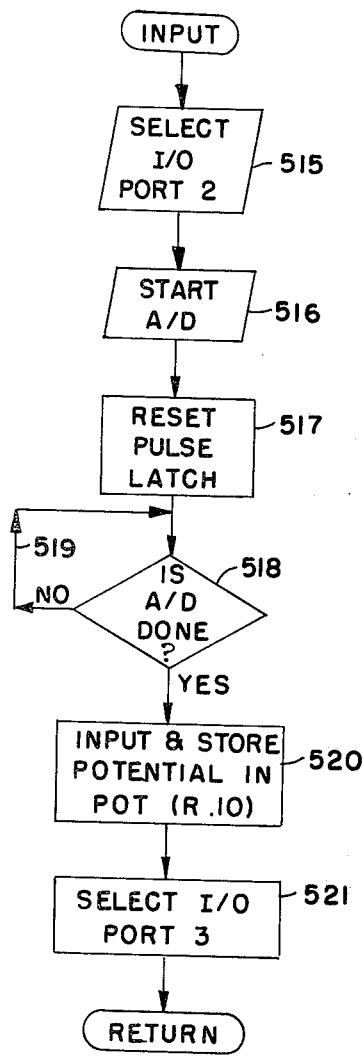

In the CPM subroutine, FIG. 20 block 514, the input potential subroutine (INPPT) of FIG. 21 is called. In the INPPT subroutine of FIG. 21, at block 515, I/O port 2 of the microcomputer 80 is selected by providing a high signal on line 209 from the latch 190 (FIG. 10) to enable the measuring circuit 249. The A/D converter 89 is started, block 516, for example by outputting a data word from decoder latch 280 that causes a high signal to occur on line 281 (FIG. 11). The CPU 170 outputs a high signal on its Q output 177 to reset the interval latch 88, block 517. The interval latch 88, then, is ready to receive the next measuring interval signal from the DMU 3.

At block 518 and loop line 519 a time delay loop is provided until the A/D conversion has been completed by the measuring circuit 249. At block 520 the output information from the A/D converter circuit 250 is input and stored in CPU 170 internal register 10 designated "POT". The inputting and storing of such potential data is effected in several steps under control, for example, of sequential multiplex control signals on lines 256, 257 (FIG. 11) to effect sequential inputting of the data words from bus 254 and bus 255 for storage in register 10.

At block 521 I/O port 3 is selected removing the high signal at line 209 (FIG. 10), thereby deenergizing the measuring circuit 249, and placing a high signal at line 208, thereby enabling the tape drive interface circuit 300 (FIG. 12) for subsequent use, if necessary. The INPPT subroutine of FIG. 21 then returns to the CPM subroutine of FIG. 20, and at block 522 a potential display subroutine (PTDSP) is called (FIG. 22).

Figure 22:
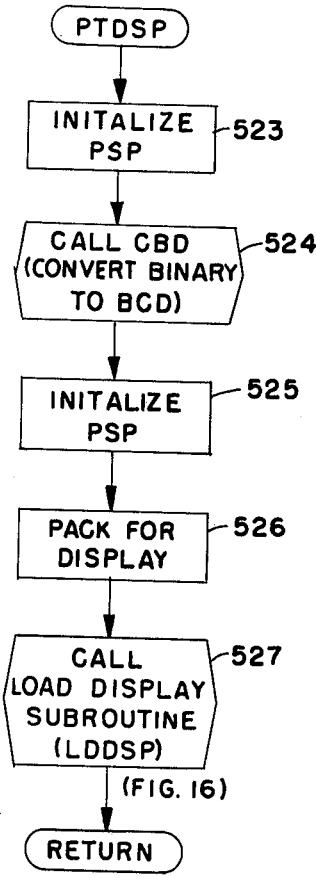
Figure 25:
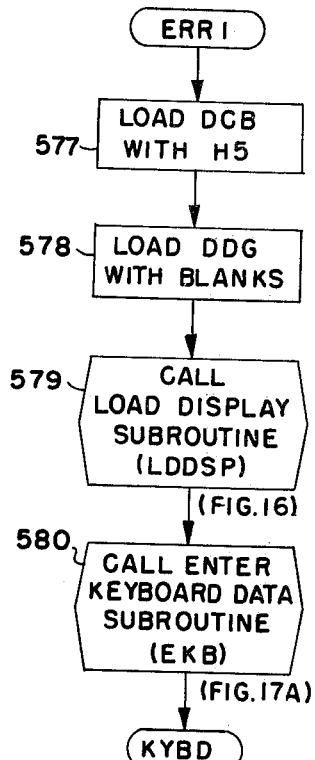

In the PTDSP subroutine of FIG. 22 at block 523 the PSP is initialized to point to the first location in the parameter stack, and at block 525 a binary to binary coded decimal conversion subroutine (CBD) is called. Such subroutine is a standard one found in RCA Manual MPM-206 and is entitled "Two's Complement To Binary Coded Decimal Conversion Subroutine." The raw data delivered directly from the A/D converter circuit 250 on buses 254, 255 is in the form of a thirteen bit two's complement number, and it is the purpose of the CBD conversion subroutine of block 524 to convert that number to binary coded decimal information for driving the respective data display digits 323-326 (FIG.

13). The first bit of such thirteen bit two's complement number, which is stored in register 10, indicates the sign of the number, and the CBD subroutine stores information concerning such sign and four binary coded decimal values, all representing such number from register 10, in five sequential memory word locations in the parameter stack.

At block 525, the PSP is initialized again, and at block 526 the four binary coded decimal data words on the parameter stack are packed into two eight bit words for storage in the DDG register 9. At block 527 the LDDSP subroutine, FIG. 16, is called to effect displaying of the potential difference just measured by the measuring circuit 249 on the four data display digits 323–326. The flow chart then returns to block 528 of the CPM subroutine in FIG. 20.

The remaining steps and loop lines 528–535 in FIG. 20 following block 514 are intended to provide a loop that ordinarily is passed 64,000 times to provide a time delay. Therefore, the measuring circuit 249, and, particularly, the A/D converter 89, is operated to obtain only about two or three measurements or conversions of the potential difference information per second; without some type of time delay provided, such conversions would occur too frequently resulting in some inaccuracies, including, for example, flickering of the display 7. Therefore, at block 528 all of the sixteen bits in the TP2 pointer, register 7, are loaded with ones. At block 529 the TP2 pointer is decremented by one, and at block 530 the lower data byte of pointer TP2 is obtained, for example, from register 7.0. An inquiry is made at block 531 to sense whether that data is zero; if not, a loop is followed via line 532 until such lower data byte becomes zero. At block 533 the higher data byte of pointer TP2 is obtained from register 7.1 and is checked at block 534 to sense whether that data is zero; if not, a loop is followed via line 535 until all of the bits in the TP2 pointer are zero. Thereafter, the CPM subroutine returns to block 540 of the ISUR subroutine in FIG. 18. Thus, as long as the operator continues to hold one of the electrodes 4 in contact with the electrolyte (soil) and until the operator presses one of the keyboard keys, the potential difference will continue to be displayed on the display 7; however, the potential difference will not yet be written on the cassette.

When the pressing of a keyboard key is sensed at block 536 of FIG. 18 in the ISUR subroutine, for example causing a low signal at the output of NAND gate 372 (FIG. 13) to be delivered via line 373 directly to the CPU 170 (FIG. 10), the flow chart follows to block 537. Thus, a keyboard input action is required from the operator for the apparatus to complete the initializing steps and to move into the potential measuring mode of operation.

At block 537 of the ISUR subroutine (FIG. 18) an inquiry is made to sense whether the keyboard 8 has been disabled. When the switch 60 is thrown to disable the keyboard, as sensed at block 537, the DCB register 8 is loaded with the code letter "P" for display at display digit 321 and a blank for display at the display digit 322, block 538. The display code "P" indicates that the apparatus 1 is operating in a potential measuring mode and that any data displayed in the data display digits 323–326 represents potential difference information actually being measured and recorded. At block 539 the LDDSP subroutine, which was described above with reference to FIG. 16, is called to effect displaying of the code in the DCB register 8.

The apparatus 1 now has been fully initialized and is prepared to commence automatic operation to sense potential difference information and to record and to display the same. Accordingly, the flow chart returns to FIG. 8, and at block 106 an inquiry is made to sense whether the keyboard 8 has been enabled. If the keyboard has not been enabled, an inquiry is made at block 107 to sense whether a measuring interval control signal has been received on the cable 51 from the DMU 3. When such a measuring interval control signal is so produced, the interval latch 88 is set to deliver a signal on line 176 to the CPU 170. At block 109 the CPU 170 then calls the potential reading subroutine (PTRDG), which is illustrated in FIG. 23 to obtain the true potential $E_T$ at the measurement location, and to display and to record the same.

Figure 23:
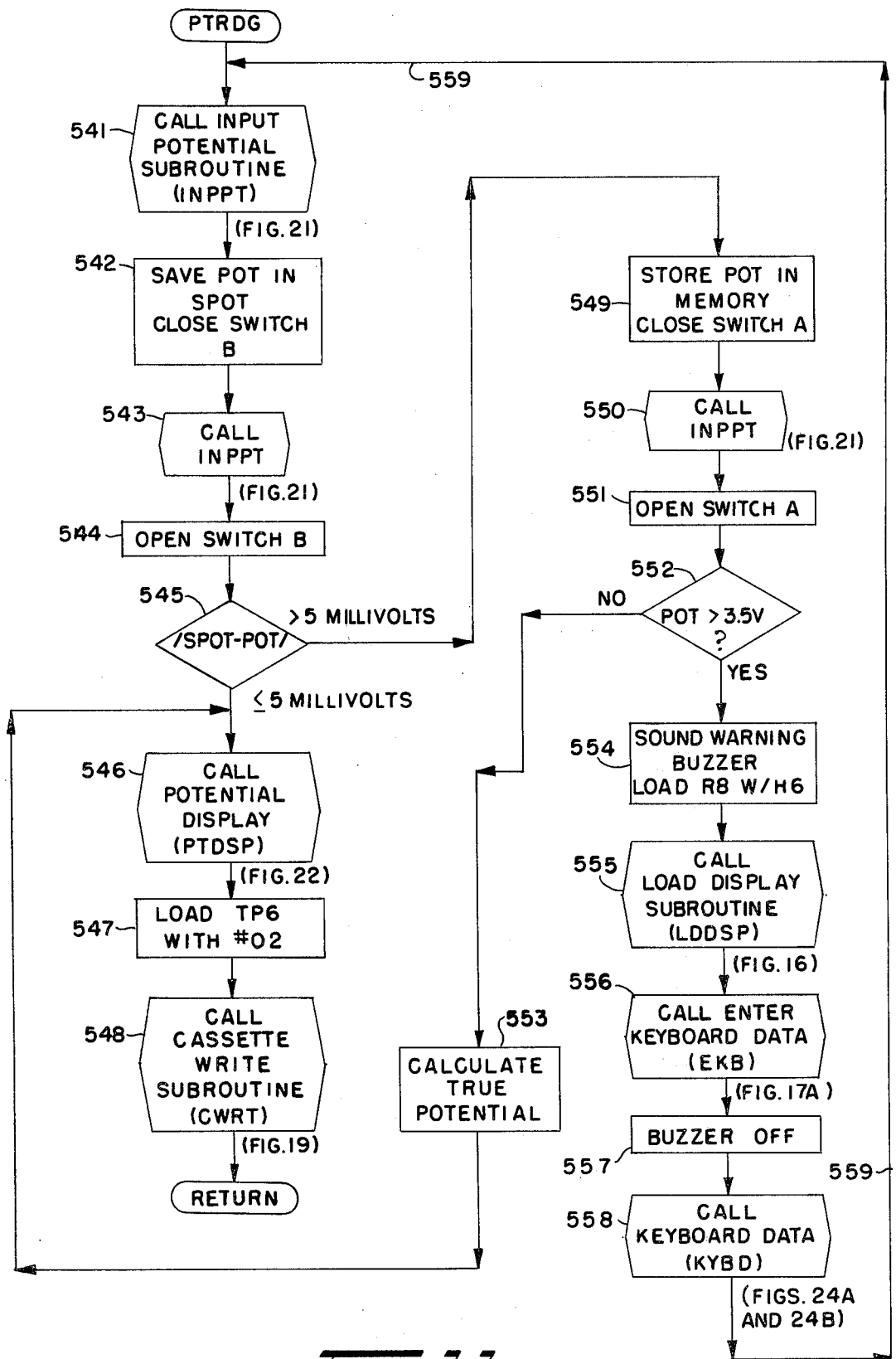

In the PTRDG subroutine of FIG. 23 at block 541 the INPPT subroutine described above with reference to FIG. 21 is called to sense the potential difference across lines 91, 92 with the switches 273A, 273B of the multiplexer 273 (FIG. 11) open. The sensed potential $E_1$ is stored in the POT register and in the parameter stack at the location addressed by the PSP. At block 542 the data word in register POT is transferred to another free register identified by SPOT, and the multiplexer switch 273B is closed to connect resistor 274B across lines 91, 92 (FIG. 11). At block 543, then, the INPPT subroutine (FIG. 21) is called again, this time storing in the POT register the second potential reading $E_2$; at block 544 the multiplexer switch 273 B is opened.

The difference between the two potentials, namely the first one $E_1$ stored in the SPOT register and the subsequent one $E_2$ stored in the POT register is checked at block 545. If the difference is less than or equal to about ±5 mv, then the flow chart follows to block 546 to call the potential display subroutine (PTDSP) of FIG. 22 to display the first potential $E_1$, as the true potential $E_T$, which is in the SPOT register and importantly in the parameter stack at the location then being addressed by the PSP. At block 547 pointer TP6, register 15, is loaded with a zero, two in order to indicate that two words stored in the parameter stack are to be written onto the cassette. These two eight bit words actually contain the information stored in the POT register which represent the binary value of the instantaneous potential then being measured by the measuring circuit 249. Thereafter, at block 548 the CWRT subroutine, FIG. 19, is called to write the two words from the parameter stack onto the cassette tape. The flow chart returns, then, from FIG. 23 back to junction 110 of FIG. 8.

However, if at block 545 in FIG. 23 the difference between the two potentials $E_1$ and $E_2$ is greater than about ±5 mv, then the third potential $E_3$ is measured. At block 549 the second potential $E_2$ then in the POT register is stored in memory, i.e. in the parameter stack at a location addressed by the PSP, and multiplexer switch 273A is closed to connect line 91 (FIG. 11) to a 15 volt supply via impedance 274A. The INPPT subroutine (FIG. 21) is called at block 550 to effect measuring of the third potential $E_3$ and then the switch 273A is opened at block 551. A comparison is made at block 552 to detect whether the third potential $E_3$ is greater than, for example, 3.5 volts. If such third potential $E_3$ does not exceed such voltage, the true potential $E_T$ is calculated at block 533 by the microcomputer 80 according to the above equation 1. The calculated true potential $E_T$ is stored in the first two locations of the parameter stack, and then the flow chart continues via blocks 546–548, as above, to display the true potential $E_T$ and to write the true potential $E_T$ onto the cassette. The flow chart then returns to junction 110 of FIG. 8.

Figure 24A:
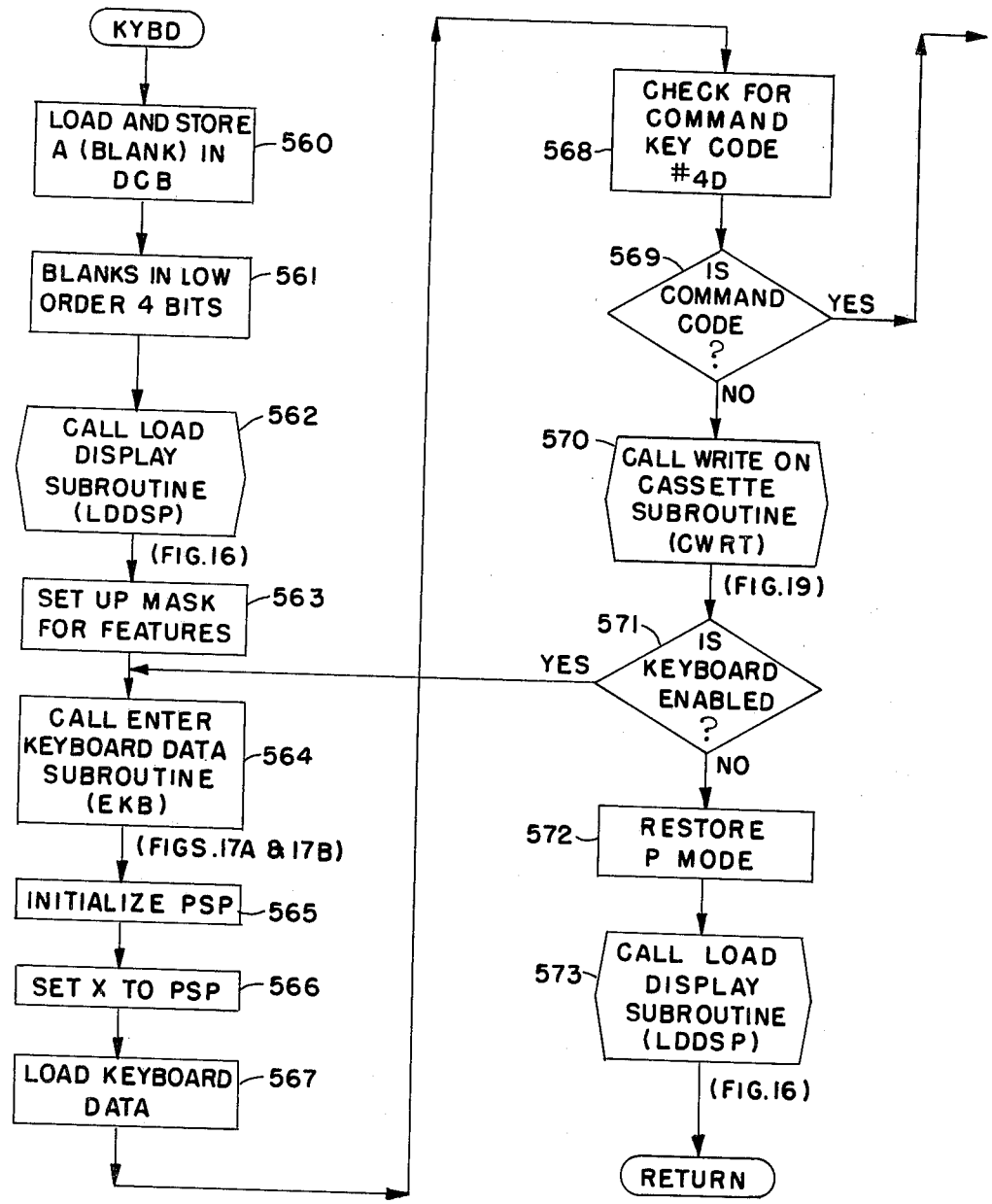
Figure 24B:
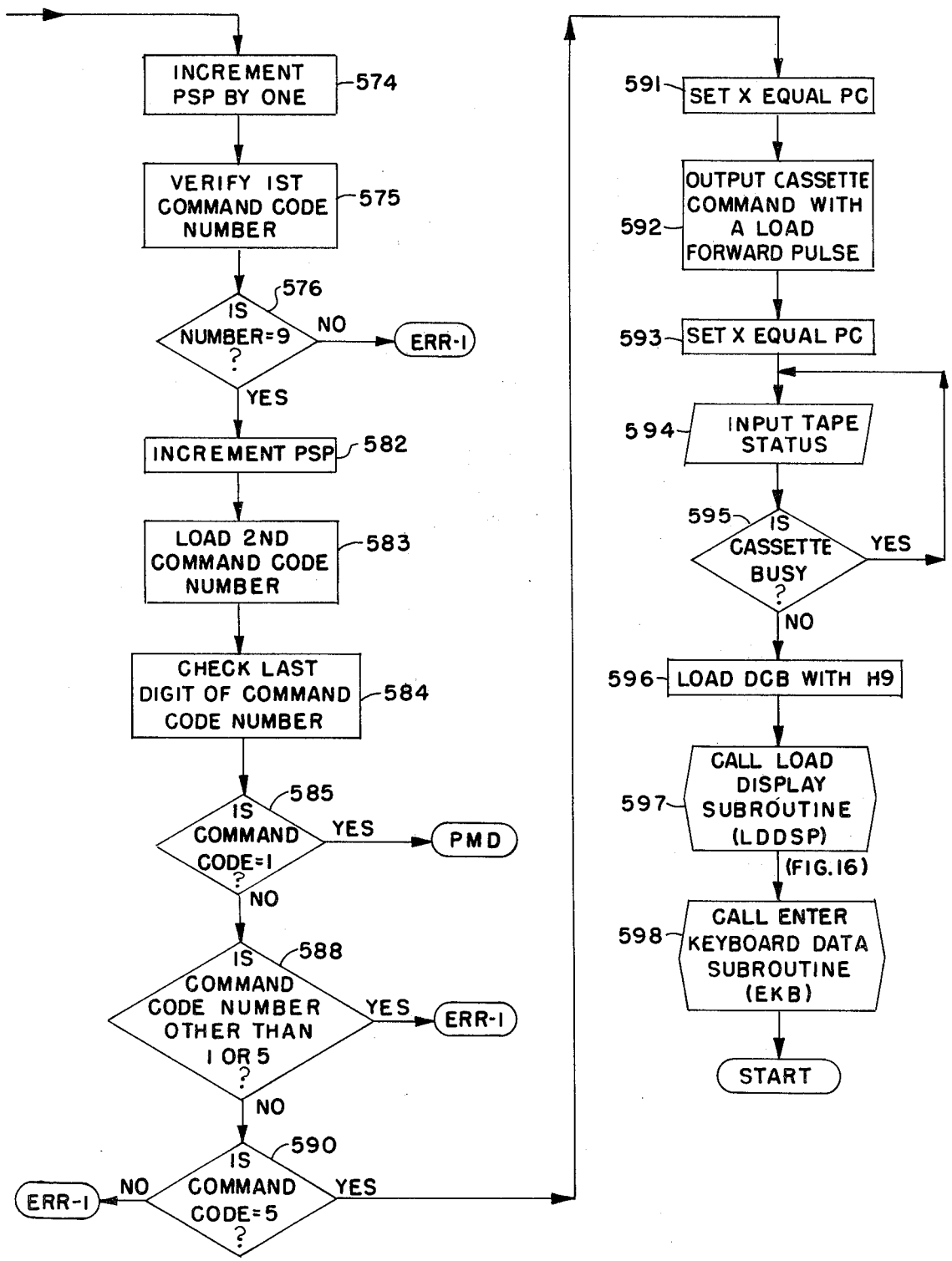

However, if in the PTRDG subroutine of FIG. 23 at block 552 the third potential reading $E_3$ exceeds about 3.5 volts, indicating a broken wire 11, the warning buzzer 215a is sounded, block 557. Also at block 554 the DCB register 8 is loaded with information that will cause the data control digits 321, 322 (FIG. 13) to display a code word "H6" indicating a broken wire. At block 555 the LDDSP subroutine is called (FIG. 16) to display the code word H6, and at block 556 the EKB subroutine of FIGS. 17A, 17B is called. The buzzer or horn 215a will continue to sound until the operator acknowledges the problem by enabling the keyboard 8 and pressing the enter key 60E to leave the EKB subroutine. Thereafter, the buzzer 215a is deactivated at block 557, and the keyboard data subroutine (KYBD) of FIGS. 24A, 24B is called at block 558. The operator then must fix the broken wire, enable the keyboard, make an appropriate keyboard entry and/or press the enter key, and disable the keyboard before the flow chart follows loop 559 back to block 541 to continue operation in the PTRDG subroutine of FIG. 23.

The KYBD subroutine is illustrated in FIGS. 24A, 24B. At block 560 a special code letter "A" and a blank are loaded and stored in DCB register 8 for display at data control digits 321, 322 to indicate that the keyboard has been enabled and that data, such as feature data, entered through the keyboard 8 ordinarily will follow. At block 561 blanks are loaded in the DDG register 9 so that the data display digits 323–326 will display blanks. At block 562 the LDDSP subroutine, FIG. 16, is called to display the code letter "A" at display digit 321 and blanks at the remaining display digits 322–326 (FIG. 13).

A feature mask to indicate that the following data will indicate features, as opposed, for example, to potential, is set up at block 563, and at block 564 the EKB subroutine, which was described above with reference to FIGS. 17A and 17B, is called to await the pressing of one or more keys on the keyboard 8. In the EKB subroutine the current keyboard data is stored on the parameter stack for subsequent recording on the cassette and display in display 7. When the enter key 60E is pressed, the EKB subroutine is left via blocks 429, 430 (FIG. 17A), with the keyboard data just entered then being displayed in the data display digits 323–326 of display 7 (FIG. 13). At block 565 (FIG. 23A) the PSP is initialized to point to the first memory word location in the parameter stack, and at block 566 the X register is set to tell the CPU 170 that the PSP in register 6 is an address of a RAM memory word location. At block 567 the keyboard data just stored via the EKB subroutine is loaded into the accumulator. More specifically, the data word stored in the parameter stack memory word location then being addressed by the PSP is loaded into the accumulator, and at block 568 a check is made to see whether such data is a command key code, such as the code "digit 4D". At block 569 an inquiry is made to sense whether such a command code has been entered on the keyboard 8; if not, at block 570 the CWRT subroutine, FIG. 19, is called to write the feature data just entered from the keyboard and stored in the parameter stack onto the cassette. At block 571 an inquiry is made to sense whether the keyboard still is enabled; if so, the steps described above in blocks 565–571 are repeated until all of the feature or fault describing information has been written onto the cassette. When the disabling of the keyboard is sensed at block 571, the automatic potential sensing, recording and displaying mode, i.e. the "P" mode, is restored at block 572 by loading in the DCB register 8 a data word that will cause the letter "P" to be displayed at display digit 321 and a blank to be displayed at display digit 322; the DDG register 9 also is loaded to cause a display of blanks at display digits 323–326. Thereafter, the LDDSP subroutine, FIG. 16, is called at block 573 to display a P and blanks, and the flow chart returns via line 559 to block 541 of PTRDG subroutine of FIG. 22.

After the broken wire has been fixed and information concerning the fault entered in the just described KYBD subroutine of FIG. 24A, the flow chart will proceed through the rest of the PTRDG subroutine of FIG. 23 in order to obtain the true potential $E_T$ and to display and to record the same. Thereafter the flow chart returns to junction 110 in FIG. 8 to continue the automatic sensing, recording, and displaying of potential difference information as described above.

Returning back to the flow chart of FIG. 8, after the PTRDG subroutine has been completed at block 109, the flow chart proceeds via a loop line 551 to junction 110 to enable continued automatic operation of the apparatus 1, as just described. Moreover, when the keyboard is enabled by switch 60, as sensed at block 106, for example to enter feature information indicating that at the immediate location in the survey a certain feature, such as a stream, fence, etc., has been encountered, the keyboard data handling subroutine (KYBD) is called at block 108. The just above described operation of the KYBD subroutine will be followed, for example, to enter feature information and to display and to record the same through blocks 560–573. The flow chart then returns to block 107 of FIG. 8.

Continuing in the KYBD subroutine of FIGS. 23A, 23B, if the keyboard data entered on the keyboard 8 is a command code, as sensed at block 569, then the PSP is incremented by one at block 574. The command code number is verified at block 575. The command code number is the number, usually a two digit number, entered on the keyboard after the command key code digit or combination of digits has been entered. According to the preferred embodiment the command code number will be a two digit number, the first digit being a 9, and the last digit being either a 1 or a 5. A last digit 1 causes the system 1 to continue sensing, measuring and displaying potential but not recording the data, e.g. while a full reel 10 of wire 11 is placed in the DMU 3. A last digit 5 means the survey of that section of buried structure has been completed, the next test lead 12 having been reached, for example; the wire 11 is then cut and a new end of wire 11 from the DMU is connected to the next test lead. The survey then may be continued. At block 575 the data word in the parameter stack location addressed by the PSP is loaded into the accumulator. At block 576 an inquiry is made to sense whether the number is "9".

If the higher order digit of the command code number is not a 9, as sensed at block 576, then the error (ERR1) subroutine is called. The ERR1 subroutine illustrated in FIG. 25 effects loading into the DCB register 8 of the CPU 170 information that will cause the data control digits 321, 322 to display a code "H5", block 577. At block 578 the DDG register 9 is loaded with information that will cause the data display digits 323-326 to display blanks. At block 579 the LDDSP subroutine from FIG. 16 is called to effect displaying of "H5" and four blanks in the display 7. The EKB subroutine, which is described above with reference to FIGS. 17A, 17B, is called at block 580 to require the operator of the apparatus to press the enter key 60E of the keyboard 8 as an acknowledgement of an error. The flow chart then returns via block 581 to the beginning of the KYBD subroutine of FIG. 24A to permit the reentering of keyboard data at block 560.

If the inquiry made at block 576 of FIG. 24B in the KYBD subroutine indicates that the first digit of the command code number is a 9, then the PSP is incremented at block 582, and the second digit of the command code number, which is stored in the memory word location of the parameter stack addressed by the PSP, is loaded into the accumulator at block 583. Such second or last digit of the command code number is checked, block 584, by inquiring whether the command code number is a 1, block 585. If the second digit of the command code number is a 1, then a potential mode (PMD) subroutine is called.

Figure 26:
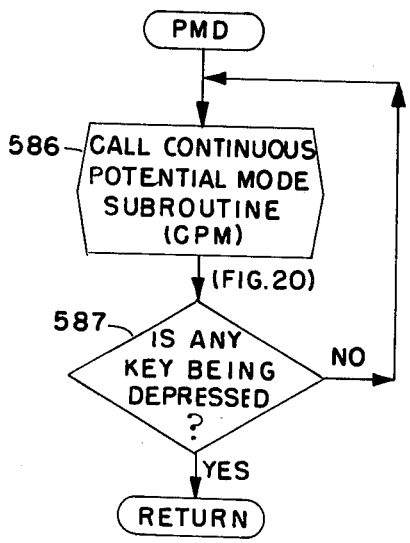

The PMD subroutine of FIG. 26 effects at block 586 calling of the CPM subroutine described above with reference to FIG. 20 to display continuously the potential difference then being sensed between the electrodes 4, which contact the electrolyte, and the buried structure, namely the pipeline 13, via the wire 11. Such potential difference will be displayed until any key on the keyboard 8 is pressed, as sensed at block 587, in response to a signal from NAND gate 372 coupled via line 373 to the CPU 170. The flow chart then returns to block 588 (FIG. 24B) of the KYBD subroutine, whereupon an inquiry is made whether the second digit of the command code number is other than a 1 or a 5. The answer to such inquiry at block 588 will be negative at this time since at block 585 it was confirmed that the command code number was a 1. A further inquiry is made at block 590 whether the second digit of the command code number is a 5; and similarly the answer there will be negative. Therefore, the flow chart follows to the ERR1 subroutine, FIG. 25, whereupon the error code H5 will be displayed in the data control digits 321, 322. Thereafter, the flow chart will return to block 560 of FIG. 24A at the beginning of the KYBD subroutine.

At the present time the command code number will be expected to be either a "91" or a "95". Therefore, at block 588, if the second digit of the command code number is other than a 1 or a 5, the flow chart follows to the ERR1 subroutine, as aforesaid.

At block 590, if the second digit of the command code number is a 5, then at block 591 the X register is set to equal the program counter in preparation for an output immediate instruction. The X register is one which tells the CPU 170 which of the sixteen internal scratch pad registers is to be used for an address register. At block 592 information is strobed into the cassette command register 303 (FIG. 12) for such register to produce briefly a pulse on one of its output lines 311 causing a load forward response in the tape drive 59. The load forward response in the tape drive generates an inter-record gap on the cassette tape indicating that the survey has been completed; for example, the next test lead location 12 has been reached. The internal electronics of the tape drive, then, power down the tape drive. The apparatus 1 then is readied for subsequent operation to survey the next section of the pipeline after the wire 11 is connected to the next test lead 12. Accordingly, at block 593 the X register is set to the PSP, and at block 594 the tape status is input to the accumulator from status register 302 (FIG. 12). An inquiry is made at block 595 to sense whether the cassette is busy, and when the cassette no longer is busy, the DCB register 8 is loaded with information that will cause the display command digits 321, 322 to display a code "H9", block 596. At block 597 the LDDSP subroutine, described above with reference to FIG. 16, is called to display the code "H9" indicating completion of that section of the survey. At block 598 the EKB subroutine described above with reference to FIGS. 17A, 17B is called to place the apparatus 1 in a wait condition until the operator presses the enter key 60E on the keyboard. Upon pressing such enter key 60E, the flow chart returns to the start block 102 of FIG. 8 to commence the next portion of the survey.

STATEMENT OF INDUSTRIAL APPLICATION

In view of the foregoing, it will be appreciated that the electrical survey apparatus and method may be employed to survey various types of buried structures, such as pipelines, power cables, telephone cables, and the like. Such structures may be buried in various types of electrolytes, such as soil, water, sand, sand beneath a body of water, etc. Moreover, the microcomputer 80, including the various portions thereof, may be used not only to effect automatic monitoring of potential difference values during a survey, but also may be employed to sense, to record, and/or to display other parameters in response to measuring interval control signals or the like delivered periodically in response to a selected parameter, such as distance, time, light intensity, temperature, etc. Using the apparatus and method of the invention a large amount of data may be obtained and conveniently analyzed and used, as desired. Of course, in the preferred embodiment, such data is used to facilitate efficient and economical cathodic protection of the buried structure.

We claim:

1. An apparatus for making electrical surveys of structures contained in an electrolyte, comprising:

electrode means contactible with the electrolyte proximate the structure, wire means for electrically connecting the apparatus with the structure at a reference location thereon, said wire means comprising a supply of wire electrically connectable at one end to a test connection of such structure, logging means for automatically electrically sensing and storing the potential difference between said electrode means and said wire means at a plurality of locations along such structure, and support means for supporting said supply and said logging means for transport along such structure, said support means comprising a distance measuring unit means for containing said supply, and distance measuring means in said distance measuring unit means for measuring the length of wire distributed from said distance measuring unit means as an indication of the distance travelled by said distance measuring unit means along such structure, and interval counter means responsive to said distance measuring means for producing interval signals at selected intervals and, therefore, at predetermined locations along such structure, and coupling means for coupling such interval signals to control said logging means to sense and store potential difference information at such locations.

2. The apparatus of claim 1 said structure being primarily buried in an earth electrolyte, and said support means being manually portable over the earth along the path of such structure.

3. The apparatus of claim 1, said support means comprising a backpack means for containing said logging means.

4. The apparatus of claim 3, said logging means comprising measuring means for measuring such potential difference, control means for controlling said measuring means to measure such potential difference at such locations, and recorder means for recording such measured potential difference information.

5. The apparatus of claim 4, further comprising set means for setting the length of each interval between adjacent locations at which potential difference measurements are made.

6. The apparatus of claim 4, further comprising data input means for manually inputting information concerning such survey to said logging means for storage by said recorder means.

7. The apparatus of claim 4, said measuring means comprising A/D converter means for converting such potential difference information to digital information for recording.

8. The apparatus of claim 7, further comprising display means for displaying the most recently read potential difference.

9. The apparatus of claim 4, said measuring means comprising A/D converter means for converting such potential difference information to digital information for recording.

10. The apparatus of claim 1, said logging means comprising measuring means for measuring such potential difference, control means for controlling said measuring means to measure such potential difference at such locations, and recorder means for recording such measured potential difference information.

11. The apparatus of claim 1, said logging means comprising an electronic means for sensing potential difference values, storage means for storing such potential difference values, and control means for controlling said electronic means and said storage means to sense and to store at such selected locations, and said support means comprising means for supporting said logging means for manual portability.

12. The apparatus of claim 11, said storage means comprising recorder means for recording such potential difference information in a magnetically responsive storage medium.

13. The apparatus of claims 11 or 12, said logging means including a housing means for protectively enclosing said electronic means and said recorder means, and further comprising power supply means in said housing means for supplying electrical power to said logging means.

14. The apparatus of claim 1, said logging means comprising a computer-type assembly.

15. The apparatus of claim 14, said computer-type assembly comprising a microprocessor and a microprocessor-controlled electronic circuit.

16. The apparatus of claim 14, further comprising program control means for controlling operation of said logging means according to a predetermined program.

17. The apparatus of claim 16, further comprising memory means for storing data during operation of said logging means.

18. The apparatus of claim 14, further comprising interval latch means for receiving interval information indicating that potential difference is to be sensed and recorded at the instant location along the structure.

19. The apparatus of claim 18, said logging means including analog to digital converter means controlled by said computer-type apparatus for converting the sensed potential at each such location to digital information and recorder means controlled by said computer-type assembly for storing such digital information.

20. The apparatus of claim 14, said logging means including analog to digital converter means controlled by said computer-type assembly for converting the sensed potential at each such location to digital information and recorder means controlled by said computer-type assembly for storing such digital information.

21. The apparatus of claim 20, further comprising verifier means controlled by said computer-type assembly for verifying the accuracy of digital information stored by said recorder means.

22. The apparatus of claim 20, further comprising display means controlled by said computer-type assembly for displaying such potential difference information as it is sensed at such locations.

23. The apparatus of claim 1, said logging means comprising measuring means for measuring the potential difference at respective locations at plural input impedances.

24. The apparatus of claim 23, wherein said measuring means comprises analog to digital converter means for converting each potential difference sensed at each location to digital information representative thereof.

25. The apparatus of claim 24, wherein said electrode means comprises electrode means continuously contactable with the electrolyte to provide continuously to an input of said analog to digital converter means the potential difference, and interval control means for causing said analog to digital converter means to convert potential difference input thereto to digital information representative thereof only at such plurality of locations along such structure.

26. A method for making structure-to-electrolyte potential difference surveys comprising the steps of:
providing a supply of elongate electrical conductor,
electrically connecting the conductor to the structure at a reference location thereon,
playing out the conductor along the structure,
contacting the electrolyte at plural test locations proximate the structure with a reference electrode, and
at substantially regularly spaced distance intervals automatically sensing and storing the potential difference at such test locations between the reference electrode and the conductor.

27. The method of claim 26, said providing comprising providing a portable supply of elongated electrical conductor.

28. The method of claim 26, said playing out comprising continuously playing out the conductor.

29. The method of claim 26, said contacting comprising continuously contacting the electrolyte along the length of the structure, including at such plural test locations.

30. The method of claim 29, said contacting comprising manually supporting at least two electrodes and walking along the path of the structure at a generally constant spaced apart distance therefrom while maintaining at least one of the electrodes continuously in contact with the electrolyte, lifting one electrode only after another has been placed in contact with the electrolyte.

31. The method of claim 26, said automatically sensing comprising automatically electrically sensing the potential difference at each test location at two different input impedances, one higher than the other.

32. The method of claim 31, further comprising sensing the difference between the two potential differences automatically sensed at each test location and, if the magnitude of such difference is lower than a predetermined amount, said storing comprising storing the potential difference sensed at the larger of the two input impedances.

33. The method of claim 26, said automatically sensing comprising converting analog potential difference information to digital information.

34. The method of claim 33, said storing comprising recording such digital information in a magnetic recording medium.

35. The method of claim 26, further comprising verifying the accuracy of the data stored with that input during said storing step.

36. The method of claim 26, further comprising inputting to a storage medium information identifying the survey and features encountered in the course of such survey.

37. The method of claim 26, further comprising displaying potential difference information automatically sensed.

38. The method of claim 37, said automatically sensing and storing comprising using a computer to effect the same, said using including self-diagnosing faults occurring during such automatically sensing and storing, and further comprising entering data concerning survey identifying information and feature information for storage, and said displaying including displaying the mode of operation of said computer in potential measuring, fault sensing, and information sensing modes.

39. The method of claim 26, further comprising sensing a fault during the survey and stopping further sensing and storing of information upon sensing such fault.

40. Apparatus for making electrical surveys of structures contained in an electrolyte by automatically sensing and storing information concerning at least one variable parameter at intervals in dependence on a second variable parameter, comprising:
sensing means for sensing the value of such one parameter,
interval means for monitoring such second parameter, said interval means including means for producing interval signals indicative of the occurrence of such respective intervals in dependence on such second parameter, and means for detecting the distance of the apparatus along the structure relative to a reference location on the latter, and
storing means responsive to the occurrence of such interval signals for automatically storing information representative of the sensed value of such one parameter.

41. The apparatus of claim 40, wherein such one variable parameter is potential difference between such structure and electrolyte at predetermined intervals along such structure.

42. The apparatus of claim 41, said sensing means comprising electrode means in contact with such electrolyte and conductor means in contact with such structure.

43. The apparatus of claim 42, said sensing means further comprising an analog to digital converter means for converting the potential difference between said electrode means and said conductor means to digital information.

44. The apparatus of claim 40, said storing means comprising means for storing information on a magnetically responsive medium.

45. The apparatus of claim 44, said storing means comprising a cassette tape drive.

46. An apparatus for making electrical surveys of structures contained in an electrolyte, comprising:
electrode means contactible with the electrolyte proximate the structure,
wire means for electrically connecting the apparatus with the structure at a reference location thereon, and
logging means for automatically electrically sensing and storing the potential difference between said electrode means and said wire means at a plurality of locations along such structure, said logging means including measuring means for measuring such potential difference, impedance changing means for changing the impedance of said measuring means at least twice at each location, and control means for controlling said measuring means to measure such potential difference at each of such impedances at each location, and recorder means for recording such measured potential difference information.

47. The apparatus of claim 46, said control means including means for establishing one of the measured potential differences at a respective location as the true potential difference at such location for storage on the basis of the difference between the magnitudes of the measured potential differences at such location.

48. The apparatus of claim 47, said control means further comprising comparator means for comparing the magnitudes of both potential differences at a respective location and for selecting the potential difference measured at the larger impedance when the difference between such magnitudes is less than a predetermined value.

49. The apparatus of claim 47, said control means further comprising comparator means for comparing the magnitudes of the potential differences measured at a respective location at two different input impedances and if the difference between the magnitudes of such measured potential differences exceeds a predetermined value for calculating the true potential for storage by said logging means on the basis of the following equation:

$$E_T = \frac{E_1 E_2 \left( \frac{R_A}{R_C} - 1 \right)}{\frac{R_A}{R_C}(E_2) - E_1}$$

wherein $E_T$ is the true potential, $E_1$ is the first measured potential difference at an input impedance $R_A$, and $E_2$ is the second measured potential difference at an input impedance of $R_C$.

50. The apparatus of claim 47, further comprising signalling means for indicating a fault condition when one of such measured potential differences exceeds a predetermined magnitude.

51. The apparatus of claim 50, further comprising shut-down means responsive to the occurrence of such a fault for stopping further operation of said logging means until correction of such fault.

52. The apparatus of claim 47, said logging means comprising a manually portable logging means.

53. An apparatus for making electrical surveys of structures contained in an electrolyte, comprising:
  electrode means contactible with the electrolyte proximate the structure,
  wire means for electrically connecting the apparatus with the structure at a reference location thereon, and
  logging means for automatically electrically sensing and storing the potential difference between said electrode means and said wire means at a plurality of locations along such structure, said logging means comprising a computer-type assembly and including analog to digital converter means controlled by said computer-type assembly for converting the sensed potential at each such location to digital information input means for receiving an input signal representative of such potential difference, impedance changing means for changing the input impedance of said input means, coupling means for coupling said input means to said analog to digital converter means, and recorder means controlled by said computer-type assembly for storing such digital information.

54. The apparatus of claim 53, said computer-type assembly including means for establishing one of the measured potential differences at a respective location as the true potential difference at such location for storage on the basis of the difference between the magnitudes of the measured potential differences at such location.

55. The apparatus of claim 54, said computer-type assembly comprising comparator means for comparing the magnitudes of both potential differences at a respective location and for selecting the potential difference measured at the larger impedance when the difference between such magnitudes is less than a predetermined value.

56. The apparatus of claim 54, said computer-type assembly comprising comparator means for comparing the magnitudes of the potential differences measured at a respective location at two different input impedances and if the differences between the magnitudes of such measured potential differences exceeds a predetermined value for calculating the true potential for storage by said logging means on the basis of the following equation:

$$E_T = \frac{E_1 E_2 \left( \frac{R_A}{R_C} - 1 \right)}{\frac{R_A}{R_C} (E_2) - E_1}$$

wherein $E_T$ is the true potential, $E_1$ is the first measured potential difference at an input impedance $R_A$, and $E_2$ is the second measured potential difference at an input impedance of $R_C$.

57. The apparatus of claim 54, further comprising signalling means for indicating a fault condition when one of such measured potential differences exceeds a predetermined magnitude.

58. The apparatus of claim 57, further comprising shut-down means responsive to the occurrence of such a fault for stopping further operation of said logging means until correction of such fault.

59. An apparatus for making electrical surveys of structures contained in an electrolyte, comprising:
  electrode means contactible with the electrolyte proximate the structure,
  wire means for electrically connecting the apparatus with the structure at a reference location thereon, and
  logging means for automatically electrically sensing and storing the potential difference between said electrode means and said wire means at a plurality of locations along such structure, said logging means comprising measuring means for measuring the potential difference at respective locations at plural input impedances, and said measuring means including impedance changing means for changing the input impedance of said measuring means.

60. The apparatus of claim 59, said impedance changing means comprising electronic switch means for controllably connecting and disconnecting at least one impedance in operative circuit relation with said measuring means and switch control means for selectively controlling connections and disconnections of said electronic switch means.

61. The apparatus of claim 60, said logging means further comprising microcomputer means for controlling the same, said microcomputer means including program control means for controlling operation of said microcomputer means to operate said switch control means at each location to obtain measurements of potential difference at plural input impedances.

62. The apparatus of claim 61, said measuring means comprising an input amplifier, and said impedance changing means comprising means for changing the input impedance of said input amplifier.

63. The apparatus of claim 61, said electronic switch means including means for selectively changing the input impedance of said $$E_T = \frac{E_1 E_2 \left( \frac{R_A}{R_C} - 1 \right)}{\frac{R_A}{R_C} (E_2) - E_1}$$

wherein $E_T$ is the true potential, $E_1$ is the first measured potential difference at an input impedance $R_A$, and $E_2$ is the second measured potential difference at an input impedance of $R_C$.

64. The apparatus of claim 63, said logging means further comprising comparator means responsive to a difference between the magnitudes of such first two measured potential differences exceeding a predetermined value and to the third potential difference being less than a further predetermined value for calculating the true potential of storage by said logging means on the basis of the following equation:

$$E_T = \frac{E_1 E_2 \left( \frac{R_A}{R_C} - 1 \right)}{\frac{R_A}{R_C}(E_2) - E_1}$$

wherein $E_T$ is the true potential, $E_1$ is the first measured potential difference at an input impedance $R_A$, and $E_2$ is the second measured potential difference at an input impedance of $R_C$, and for stopping further measurements by said logging means when the magnitude of the measured potential difference at said third input impedance exceeds such further predetermined value indicating a fault condition in said wire means.

65. The apparatus of claim 64, further comprising audible alarm means for indicating such fault and manually operable input means for controlling said microcomputer means to disable said alarm means.

66. The apparatus of claims 60 or 61, wherein said measuring means comprises analog to digital converter means for converting each potential difference sensed at each location to digital information representative thereof.

67. The apparatus of claim 66, wherein said electrode means comprises electrode means continuously contactable with the electrolyte to provide continuously to an input of said analog to digital converter means the potential difference, and interval control means for causing said analog to digital converter means to convert potential difference input thereto to digital information representative thereof only at such plurality of locations along such structure.

68. A method for making structure-to-electrolyte potential difference surveys comprising the steps of:
providing a supply of elongate electrical conductor,
electrically connecting the conductor to the structure at a reference location thereon,
playing out the conductor along the structure,
contacting the electrolyte at plural test locations proximate the structure with a reference electrode, and
automatically sensing and storing the potential difference at such test locations between the reference electrode and the conductor, said automatically sensing comprising automatically electrically sensing the potential difference at each test location at two different input impedances, one higher than the other, sensing the difference between the two potential differences automatically sensed at each test location and, if such difference is larger than a predetermined value, said automatically sensing further comprising sensing the potential difference at such test location at an input impedance of a still smaller magnitude, and if the value of the potential difference sensed in the latter step is less than a predetermined amount, then calculating a true potential difference $E_T$ according to the equation:

$$E_T = \frac{E_1 E_2 \left( \frac{R_A}{R_C} - 1 \right)}{\frac{R_A}{R_C}(E_2) - E_1}$$

wherein $E_T$ is the true potential, $E_1$ is the first measured potential difference at an input impedance $R_A$, and $E_2$ is the second measured potential difference at an input impedance of $R_C$, and said storing including storing such true potential difference as that sensed at such test location.

69. The method of claim 68, wherein if the value of the latter second potential difference at the lowest input impedance exceeds a predetermined amount, indicating a fault condition and stopping the survey.

70. The method of claim 69, further comprising repairing the fault and then repeating the preceding steps.

71. A method for making structure-to-electrolyte potential difference surveys comprising the steps of:
providing a supply of elongate electrical conductor,
electrically connecting the conductor to the structure at a reference location thereon,
playing out the conductor along the structure,
contacting the electrolyte at plural test locations proximate the structure with a reference electrode,
automatically sensing and storing the potential difference at such test locations between the reference electrode and the conductor, and sensing a fault during the survey, stopping further sensing and storing of information upon sensing such fault, and automatically diagnosing the nature of such a fault and displaying the nature of such fault.

72. The method of claim 71, further comprising correcting such fault and entering restart information to recommence the aforesaid steps.

73. A method for making structure-to-electrolyte potential difference surveys comprising the steps of:
providing a supply of elongate electrical conductor,
electrically connecting the conductor to the structure at a reference location thereon,
playing out the conductor along the structure,
contacting the electrolyte at plural test locations proximate the structure with a reference electrode,
automatically sensing and storing the potential difference at such test locations between the reference electrode and the conductor, and using the potential difference information stored as a guide for effectively and efficiently cathodically protecting the structure.

74. An apparatus for making electrical surveys of structures contained in an electrolyte, comprising:
electrode means contactible with the electrolyte proximate the structure, said electrode means comprising electrode means for assuring continuous connection with the electrolyte, and including a plurality of manually portable electrodes and means for electrically connecting the same in electrical parallel relation,
wire means for electrically connecting the apparatus with the structure at a reference location thereon, and
logging means for automatically electrically sensing and storing the potential difference between said electrode means and said wire means at a plurality of substantially regularly spaced locations along such structure.

75. The apparatus of claim 74, said wire means comprising a supply of wire electrically connectable at one end to such structure, support means for supporting said supply and said logging means for transport along such structure, said logging means comprising measuring means for measuring such potential difference, control means for controlling said measuring means to measure such potential difference at such locations, and recorder means for recording such measured potential difference information.

76. An apparatus for making electrical surveys of structures contained in an electrolyte, comprising:
  electrode means contactible with the electrolyte proximate the structure,
  wire means for electrically connecting the apparatus with the structure at a reference location thereon, and
  logging means for automatically electrically sensing and storing the potential difference between said electrode means and said wire means at a plurality of locations along such structure, and
  said logging means comprising analog to digital converter means for converting the sensed potential difference at each location to a digital value and recorder means for storing such digital values, and automatic control means for operating said analog to digital converter means and recorder means to obtain such digital values and to store the same at predetermined intervals along such structure.

77. The apparatus of claim 76, further comprising interval control means for producing interval signals at selected distances along such structure, and means for coupling such interval signals to said automatic control means for causing the same to operate said analog to digital converter means and recorder means at such locations.

78. The apparatus of claim 77, wherein said electrode means comprises electrode means for maintaining a substantially continuous contact with such electrolyte.

79. The apparatus of claim 78, wherein said electrode means, wire means and logging means are transportable along such structure, said wire means comprising a supply of wire, and said interval control means comprising means for measuring the length of wire payed out from said supply as the latter is transported along such structure.

80. The apparatus of claim 79, further comprising adjustable means for determining the length of intervals at which potential difference information is sensed and automatically recorded.

81. The apparatus of claim 77, further comprising display means for displaying the values of potential difference sensed by said logging means.

82. The apparatus of claim 81, said display means including means for displaying information concerning the mode of operation of the apparatus, including operation in potential sensing mode, initializing mode, and fault mode.

83. The apparatus of claim 76, further comprising means for setting said logging means to commence such sensing and storing.

84. An apparatus for making electrical surveys of structures contained in an electrolyte, comprising:
  electrode means contactible with the electrolyte proximate the structure,
  wire means for electrically connecting the apparatus with the structure at a reference location thereon,
  logging means for automatically electrically sensing and storing the potential difference between said electrode means and said wire means at a plurality of locations along such structure, and
  data entry means for entering information into said logging means, said data entry means comprising a keyboard, program control means responsive to information entered by said keyboard for entering feature information into said storage means and for controlling operation of said logging means.

85. The apparatus of claim 84, said data entry means further comprising enabling means for selectively enabling and disabling said keyboard.

86. An apparatus for making electrical surveys of structures contained in an electrolyte, comprising:
  electrode means contactible with the electrolyte proximate the structure,
  wire means for electrically connecting the apparatus with the structure at a reference location thereon,
  logging means for automatically electrically sensing and storing the potential difference between said electrode means and said wire means at a plurality of locations along such structure, and,
  keyboard display unit means coupled to said logging means for manually entering feature data and control signals to said logging means for storage thereby and for displaying information so entered and potential difference information as it is sensed automatically by said logging means.

87. A method for making structure-to-electrolyte potential difference surveys comprising the steps of:
  providing a supply of elongate electrical conductor,
  electrically connecting the conductor to the structure at a reference location thereon,
  playing out the conductor along the structure,
  contacting the electrolyte at plural test locations proximate the structure with a reference electrode,
  automatically sensing and storing the potential difference at such test locations between the reference electrode and the conductor,
  transporting the supply of conductor, the reference electrode, and automatic sensing and storing equipment along the structure, and
  automatically sensing the distance thereof along the structure with respect to a reference location, and
  said sensing distance comprising producing interval signals representative of discrete intervals travelled along the structure and said automatically sensing comprising automatically sensing potential difference in response to the occurrence of respective interval signals.

88. The method of claim 87, further comprising continuously moving the supply of conductor, reference electrode, and equipment for automatically sensing and storing along the structure.

89. The method of claim 87, wherein the structure is buried in electrolyte including soil, and continuously walking on the electrolyte along the path of the structure while manually carrying the supply of conductor, reference electrode, and equipment for automatically sensing and storing.

90. The method of claim 87, further comprising setting specific intervals at which potential difference is to be sensed along the structure.

91. An apparatus for making electrical surveys of structures contained in an electrolyte, comprising:
  electrode means contactible with the electrolyte proximate the structure,
  wire means for electrically connecting the apparatus with the structure at a reference location thereon, and
  logging means for automatically electrically sensing and storing the potential difference between said electrode means and said wire means at a plurality of locations along such structure, said logging means including a storage medium and a circuit for storing and verifying data in such storage medium, including input data means for receiving data concerning a potential difference sensed by said logging means and delivering the same to said storage medium, delivery means for delivering data to said input data means, command means for commanding operation of said storage medium to store such data from said data input means, data read means for reading the data in said storage medium, and comparator means for comparing such data read by said data read means with that delivered by said delivery means to verify the accuracy of the data stored in said storage medium.

92. The apparatus of claim 91, further comprising control means responsive to the inability of said comparator means to verify the accuracy of the data stored in said storage medium for controlling said command means, data read means and comparator means to repeat their sequential operations until the data stored in said storage medium is verified.

93. The apparatus of claim 91, said input data means comprising a data storage register.

94. The apparatus of claim 93, said data storage register comprising an electronically responsive latch.

95. The apparatus of claim 93, said delivery means comprising a multiple circuit electrical bus.

96. The apparatus of claim 95, further comprising a microcomputer also coupled to said bus for controlling the delivery of data thereon.

97. The apparatus of claim 93, said command means comprising a command register.

98. The apparatus of claim 97, said command register comprising an electronically responsive latch.

99. The apparatus of claim 93, said data read means comprising a data read register.

100. The apparatus of claim 99, further comprising microcomputer means for controlling operation of said storage data register and said data read register and said comparator means comprising program control means for said microcomputer for comparing the information from said registers.

101. The apparatus of claim 93, further comprising status register means for storing information indicative of the operational status of said storage medium, and bus means for connecting said microcomputer means to said registers for controlling the same and said storage medium.

102. The apparatus of claim 101, said storage medium comprising a tape drive for storing information on a magnetically responsive material.

* * * * *